(12) United States Patent
Niu et al.

(10) Patent No.: US 7,763,779 B2
(45) Date of Patent: Jul. 27, 2010

(54) MAIZE STRESS-RESPONSIVE PROMOTER

(75) Inventors: Xiping Niu, Johnston, IA (US);
Nicholas J Bate, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/485,321

(22) Filed: Jun. 16, 2009

(65) Prior Publication Data

US 2009/0260111 A1    Oct. 15, 2009

Related U.S. Application Data

(62) Division of application No. 12/254,268, filed on Oct. 20, 2008.

(60) Provisional application No. 60/981,228, filed on Oct. 19, 2007.

(51) Int. Cl.
*A01H 5/00* (2006.01)
*C12N 5/04* (2006.01)
*C12N 15/63* (2006.01)
*C07H 21/04* (2006.01)

(52) U.S. Cl. .................. 800/298; 435/320.1; 435/419; 536/24.1

(58) Field of Classification Search .................. None
See application file for complete search history.

(56) References Cited

U.S. PATENT DOCUMENTS 5,990,387 A * 11/1999 Tomes et al. ................ 800/293
2007/0192889 A1   8/2007 LaRosa et al.

FOREIGN PATENT DOCUMENTS

| EP | 1 835 028 A1 | 9/2007 |
| WO | 2006066498 A1 | 6/2006 |
| WO | 2006124752 A2 | 11/2006 |

OTHER PUBLICATIONS

Wilson et al. (NCBI, GenBank Sequence Accession No. AC186900, Published May 27, 2006).*
Hu, et al.; "Overexpressing a NAM, ATAF, and CUC (NAC) transcription factor enhances drought resistance and salt tolerance in rice"; PNAS (Aug. 29, 2006) 103(35):12987-12992; National Academy of Sciences; Washington, DC, US.
Tran, et al.; "Isolation and Functional Analysis of Arabidopsis Stress-Inducible NAC Transcription Factors That Bind to a Drought-Resistance cis-Element in the early responsive to dehydration stress 1 Promoter"; The Plant Cell (Sep. 2004) 16:2481-2498; American Society of Plant Biologists; Rockville, MD, US.
Fujita, et al.; "A dehydration-induced NAC protein, RD26, is involved in a novel ABA-dependent stress-signaling pathway"; The Plant Journal (2004) 39:863-876; Blackwell Publishing Ltd.; Oxford, UK.
Hegedus, et al.; "Molecular characterization of *Brassica napus* NAC domain transcriptional activators induced in response to biotic and abiotic stress"; Plant Molecular Biology (2003) 53:383-397; Kluwer Academic Publishers, The Netherlands.
Straub, et al.; "Structure and promoter analysis of an ABA- and stress-regulated barley gene, HVA1"; Plant Molecular Biology (1994) 26:617-630; Kluwer Academic Publishers; Belgium.
Kikuchi, et al.; "Molecular Analysis of the NAC gene family in rice"; Mol Gen Genet (2000) 262:1047-1051; Springer; Berlin/Heidelberg Germany.
Nakashima, et al.; "Functional analysis of a NAC-type transcription factor OsNAC6 involved in abiotic and biotic stress-responsive gene expression in rice"; The Plant Journal (2007) 51:617-630; Blackwell Publishing Ltd.; Oxford, UK.

* cited by examiner

*Primary Examiner*—Vinod Kumar

(57) ABSTRACT

Methods and compositions for modulating plant development are provided. Polynucleotide sequences encoding ZmSNAC polypeptides are provided, as are the amino acid sequences of the encoded polypeptides. The sequences can be used in a variety of methods including modulating root development, modulating floral development, modulating leaf and/or shoot development, modulating senescence, modulating seed size and/or weight, and modulating tolerance of plants to abiotic stress. Transformed plants, plant cells, tissues, and seed are also provided. A stress-inducible ZmSNAC1 promoter is also provided.

4 Claims, 2 Drawing Sheets

```
               321       330        340        350        360        370        380        390        400
         (321)  321                                                                                         
         ANAC   (266) VVPNLEYNCGYLKTEEEVESSHGFNNSGELAQKGYGVDSFGYSGQVGGFGFM-------------------------------
         ATAF2  (241) SSMELLQPDAFVPQFLYQS--DYFTSFQDPPEQ---KPFLNWSFAPQG--------------------------------
         ATAF1  (251) LDFGFNYIDATVDNAFG------GGGSSNQMFPL---QDMFMYMQKPY---------------------------------
         NAP    (243) -E-------------------------SSWFGDLQFNQDEILNHHRQAMFKF----------------------------
         AtNAM  (282) PSKRFNGGG-----VG-------DCSTSMAATPLMQNQGGIYQLPGLNWYS------------------------------
         TIP    (286) HNEDYIQTQYGTNDADEYMSKFLDSFLDIPYEPEQIPYEPQNLSSCNKINDESKRGIKIRARRAQAPGCAEQFVMQGDAS
         CUC2   (300) RNVSTQSNFRSFQENFNQFPYFGSSASTMTSAVNLPSFQGGGGVSGMNYWLPATAEENESKVGVLHAGLDCIWNY----
         CUC1   (271) AAAAFFPNLPSLPPTVLPPPSFAMYGGGSPAVSVWPFTL-----------------------------------------
         CUC3   (272) EDDFDFNLGVKTEQSSNGNEIDVRDYLENPLFQEASYGLLGFSSSPGPLHMLLDSPCPLGFQL-----------------
         NAC1   (270) LDSFCSSDQMVLRALLSQLTKIDGSLGPKESQSYGEGSSESLLTDIGIPSTVWNC-------------------------
         ZM-SNAC1 (266) LSYDDIQGMYSGLDMLPPPGEDFYSSLFASPRVKGNQPAGAAGLGQF------------------------------
         ZM-SNAC2 (246) LSYDDIQGMYSGLDMLPPPGEDFYSSLFASPRVRGNQPTGAAGLGPF------------------------------
         ZM-SNAC3 (256) LSYDDIQGMYSGLDMLPAGEDLYSSLFASPRVRGNQPTGPAGLGPF-------------------------------
         ZM-SNAC5 (298) INPAGSMLGLGGHQLGSAA--VGVGLPAGDPLL----QDILTYWGKPY---------------------------------
         ZM-SNAC4 (264) VNPAGSMLDP-------------VVGHAGGDPLL----QDILMYWGKPF---------------------------------
         Consensus (321) L                          SS     A    P   V                      F
```

FIGURE 1

MAIZE STRESS-RESPONSIVE PROMOTER

CROSS REFERENCE

This application is a divisional of U.S. Utility patent application Ser. No. 12/254,268 which was filed on Oct. 20, 2008 which claims priority to U.S. Provisional Patent Application Ser. No. 60/981,228 filed Oct. 19, 2007, both of which are incorporated herein by reference.

FIELD OF THE INVENTION

The invention relates to the field of genetic manipulation of plants, particularly the modulation of gene activity to affect plant development and growth.

BACKGROUND OF THE INVENTION

Drought tolerance is a complex trait, controlled by multiple genes. Gene switches such as transcription factors, which can have significant and specific effects on plant physiology, are desirable modulation targets. Stress-responsive NAC transcription factors (SNACs) may control expression of numerous downstream genes important for adaptation to drought stresses and may ultimately enhance drought tolerance through one or more mechanisms such as stomatal aperture reduction, delayed senescence, and increased sink and source strength. It has been shown that ABA- and drought-responsive NACs can enhance drought tolerance in *Arabidopsis* (Tran, et al., (2004) *Plant Cell* 16:2481-2498) and rice (Hu, et al., (2006) *PNAS* 103(35):12987-12992). Therefore, SNAC genes from maize may also be used individually or in combination with other genes to enhance drought tolerance.

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs is desired, tissue-specific or tissue-preferred promoters may be used. That is, they may drive expression exclusively or preferentially in specific tissues or organs. Such tissue-specific promoters may be temporally constitutive or inducible. In any case, additional regulatory sequences upstream and/or downstream from a core promoter sequence may be included in expression constructs of transformation vectors to bring about varying levels of expression of heterologous nucleotide sequences in a transgenic plant.

As this field develops and more genes become accessible, a greater need exists for plants transformed with multiple genes. These multiple exogenous genes typically need to be controlled by separate regulatory sequences. Further, some genes should be regulated constitutively whereas other genes should be expressed at certain developmental stages or locations in the transgenic organism. Accordingly, a variety of regulatory sequences having diverse effects is needed.

Multiple regulatory sequences are also needed in order to avoid undesirable molecular interactions which can result from using the same regulatory sequence to control more than one gene.

The inventor herein discloses the isolation and characterization of a promoter associated with a transcription factor which can serve as a regulatory element for expression of isolated nucleotide sequences of interest, thereby impacting various traits in plants. Alternatively or additionally, the promoter may be used to drive scorable markers.

BRIEF SUMMARY OF THE INVENTION

Compositions and methods of the invention comprise and employ maize SNAC transcription factors that are involved in modulating plant development, morphology and physiology. Compositions further include expression cassettes and vectors comprising the ZmSNAC sequences of the invention, and plants, plant cells and plant parts in which ZmSNAC expression is modified. The plants, plant cells and plant parts of the invention may exhibit enhanced abiotic stress tolerance through such phenotypic changes as delayed leaf rolling, reduced transpiration rate, increased stomatal closure and improved cell membrane stability, all relative to a plant, plant cell or plant part not modified per the invention.

Methods are provided for modifying the level of a ZmSNAC polypeptide in a plant comprising introducing into the plant a selected polynucleotide. The polynucleotide may be introduced within a construct designed to modulate the level or activity of the ZmSNAC polypeptide throughout the plant or in targeted tissues or at targeted developmental stages.

BRIEF DESCRIPTION OF THE DRAWINGS

FIG. 1 provides an amino acid alignment of NAC transcription factors from various species. Included are ANAC (At1g52890, SEQ ID NO: 12); ATAF2 (At5g08790, SEQ ID NO: 13); ATAF1 (At1g01720, SEQ ID NO: 14); NAP (At1g69490, SEQ ID NO: 15); AtNAM (At1g52880, SEQ ID NO: 16); TIP (At5g24590, SEQ ID NO: 17); CUC2 (At5g53950, SEQ ID NO: 18); CUC1 (At3g15170, SEQ ID NO: 19); CUC3 (At1g76420, SEQ ID NO: 20); *Arabidopsis* NAC1 (At1g56010, SEQ ID NO: 21); ZmSNAC1 (SEQ ID NO: 2); ZmSNAC2 (SEQ ID NO: 4); ZmSNAC3 (SEQ ID NO: 6); ZmSNAC5 (SEQ ID NO: 10); ZmSNAC4 (SEQ ID NO: 8) and a consensus (SEQ ID NO: 22).

BRIEF DESCRIPTION OF THE SEQUENCES

Figure 2:
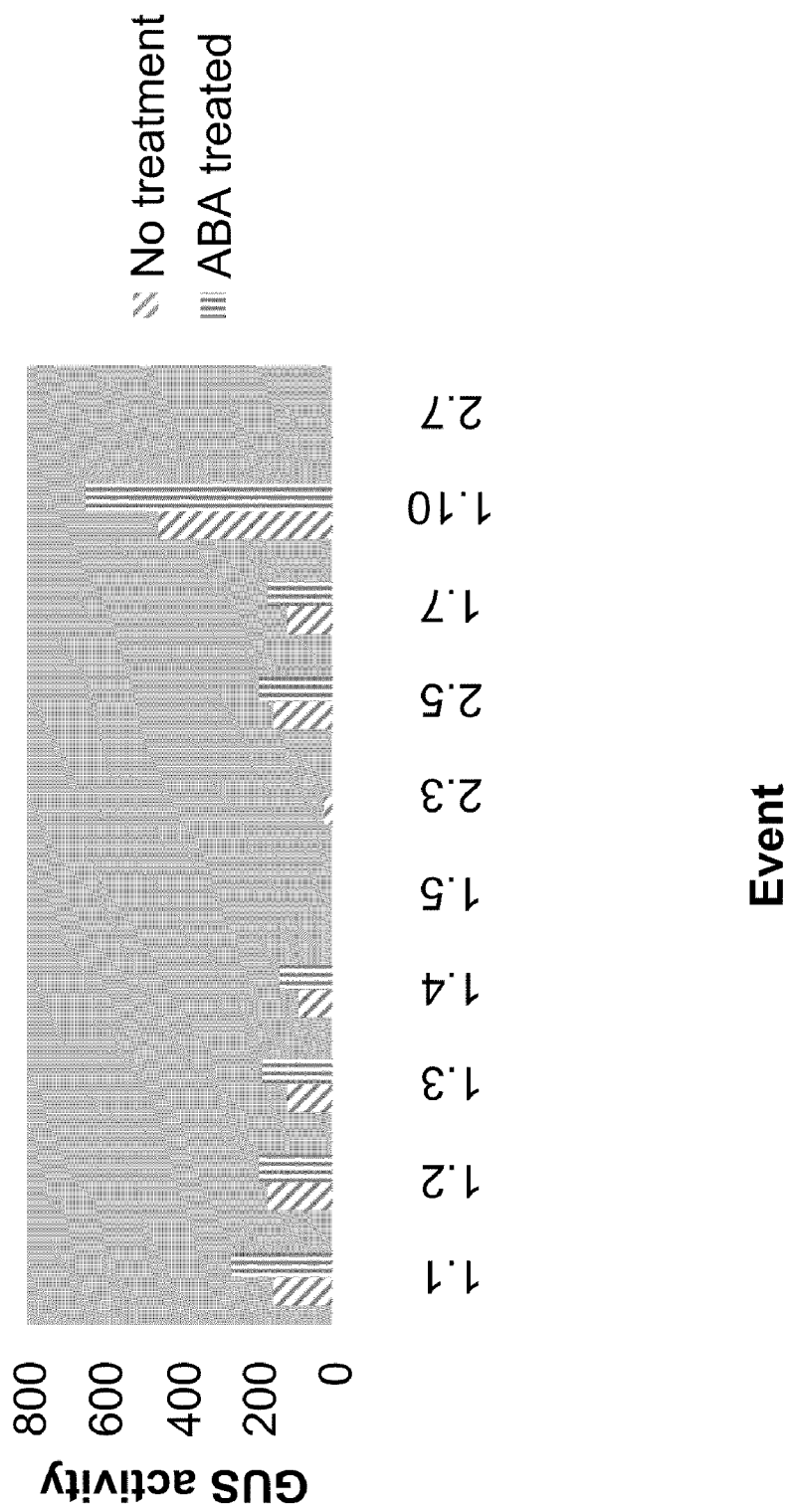
FIG. 2 shows GUS expression driven by the ZmSNAC1 promoter.

SEQ ID NO: 1 and 2 provide nucleotide and amino acid sequences for ZmSNAC1.

SEQ ID NO: 3 and 4 provide nucleotide and amino acid sequences for ZmSNAC2.

SEQ ID NO: 5 and 6 provide nucleotide and amino acid sequences for ZmSNAC3.

SEQ ID NO: 7 and 8 provide nucleotide and amino acid sequences for ZmSNAC4.

SEQ ID NO: 9 and 10 provide nucleotide and amino acid sequences for ZmSNAC5.

SEQ ID NO: 11 provides ZmSNAC1 promoter sequence.

SEQ ID NOS: 12 through 21 provide *Arabidopsis* NAC proteins as noted in the brief description of the drawings.

SEQ ID NO: 22 provides a consensus of *Arabidopsis* and *Zea mays* NAC proteins.

DETAILED DESCRIPTION OF THE INVENTION

The present invention now will be described more fully with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Compositions

Compositions of the invention include maize SNAC transcription factor polypeptides and polynucleotides that are involved in modulating plant development, morphology and physiology. In particular, the present invention provides for isolated polynucleotides comprising nucleotide sequences encoding the amino acid sequences shown in SEQ ID NO: 2, 4, 6, 8 and 10. Further provided are isolated polypeptides having an amino acid sequence encoded by a polynucleotide described herein, for example those set forth in SEQ ID NO: 1, 3, 5, 7 and 9.

NAC transcription factors are encoded by genes present in a wide range of plant species, the name being derived from the NAM (no apical meristem; Souer, et al., (1996) *Cell* 85:159-170), ATAF1,2 and CUC2 (cup-shaped cotyledon 2; Aida, et al., (1997) *Plant Cell* 9:841-857) transcription factors. Expression patterns of NAC transcription factors, and the mutant phenotypes conferred by modulation of their expression, are similar. A highly conserved N-terminal DNA-binding domain has been identified and its structure has been characterized (Ernst, et al., (2004) *EMBO Reports* 5(3):297-303). The more diverse C-terminal regions comprise transcriptional activation domains (Xie, et al., (2000) *Genes Dev.* 14:3024-3036; Duval, et al., (2002) *Plant Mol. Bio.* 50:237-248). NAC transcription factors have been shown to interact with numerous genes involved in meristem formation, organ differentiation, auxin signalling, root growth and in biotic and abiotic stress response (see, review by Olsen, et al., (2005) *Trends in Plant Science* 10(2):1360-1385). A NAC recognition sequence (NACRS), and a core binding sequence, have been identified in *Arabidopsis* (Tran, et al., (2004) *Plant Cell* 16:2481-2498).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides and up to the full-length polynucleotide encoding the proteins of the invention.

A fragment of a ZmSNAC polynucleotide that encodes a biologically active portion of a NAC transcription factor of the invention will encode at least 15, 25, 30, 50, 100, 150, 200, 225, 250, 275, 300 or 339 contiguous amino acids, or up to the total number of amino acids present in a full-length polypeptide of the invention. Fragments of a SNAC polynucleotide that are useful as hybridization probes or PCR primers generally need not encode a biologically active polyeptide.

Thus, a fragment of a ZmSNAC polynucleotide may encode a biologically active portion of a SNAC transcription factor, or it may be a fragment that can be used as a hybridization probe or PCR primer using methods disclosed below. A biologically active portion of a SNAC transcription factor can be prepared by isolating a portion of one of the ZmSNAC polynucleotides of the invention, expressing the encoded portion of the ZmSNAC protein (e.g., by recombinant expression in vitro) and assessing the activity of the encoded portion. Activity could be assessed by DNA binding activity or protein interaction studies, and/or by expressing the ZMSNAC or portions of the protein in transgenic plants and evaluating the plants for a phenotype.

Polynucleotides that are fragments of a ZmSNAC nucleotide sequence comprise at least 16, 20, 50, 75, 100, 150, 200, 250, 300, 350, 400, 450, 500, 550, 600, 650, 700, 800, 900 or 1000 contiguous nucleotides or up to the number of nucleotides present in a full-length ZmSNAC polynucleotide disclosed herein.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those which, because of the degeneracy of the genetic code, do not change the encoded amino acid sequence. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a ZmSNAC protein of the invention.

Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 2, 4, 6, 8 or 10 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Certain variant proteins encompassed by the present invention are biologically active, that is, they continue to possess the desired biological activity of the native protein, i.e., transcription factor activity, as described herein. Such variants may result from, for example, genetic polymorphism or human manipulation. Biologically active variants of a native SNAC protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations, and insertions. Methods for such manipulations are generally known in the art. For example, amino acid sequence variants and fragments of the SNAC proteins can be prepared by mutations in the DNA. Methods for mutagenesis and polynucleotide alterations are well known in the art. See, for example, Kunkel, (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired transcription factor activity. Obviously, the mutations that will be made in the DNA encoding the variant must not place the sequence out of reading frame and optimally will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. That is, the activity can be evaluated by assaying for DNA binding activity or protein-protein interactions, the activation of gene expression in transient studies, or an effect on gene expression in transgenic plants.

Variant polynucleotides and proteins also encompass sequences and proteins derived from a mutagenic or recombinogenic procedure such as DNA shuffling. With such a procedure, one or more different NAC coding sequences can be manipulated to create a new NAC polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a ZmSNAC gene of the invention and other known NAC genes to obtain a new gene coding for a protein with an improved property of interest. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; PCT Publication Number WO97/20078 and U.S. Pat. Nos. 5,605,793 and 5,837,458.

By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences of the present invention regulate (i.e., repress or activate) transcription.

The polynucleotides of the invention can be used to isolate corresponding sequences from other organisms, particularly other plants, more particularly other monocots. In this manner, methods such as PCR, hybridization and the like can be used to identify such sequences based on their sequence homology to the sequences set forth herein. Sequences isolated based on their sequence identity to the entire NAC sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode a NAC protein and which hybridize under stringent conditions to the SNAC sequences disclosed herein, or to variants or fragments or complements thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides, and may be labeled with a detectable group such as $^{32}P$, or any other detectable marker. Thus, for example, probes for hybridization can be made by labeling synthetic oligonucleotides based on the ZmSNAC polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire ZmSNAC polynucleotide disclosed herein, or one or more portions thereof, may be used as a probe capable of specifically hybridizing to corresponding NAC polynucleotides. To achieve specific hybridization under a variety of conditions, such probes include sequences that are unique among NAC polynucleotide sequences and are optimally at least about 10 nucleotides in length and most optimally at least about 20 nucleotides in length. Such probes may be used to amplify corresponding NAC polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2 and the BLOSUM62 scoring matrix.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The invention further provides plants having altered levels and/or activities of the ZmNAC polypeptides of the invention. In some embodiments, a construct directing increased expression of the sequences of the invention is stably incorporated into the genome of a plant of the invention. Other embodiments provide plants that are genetically modified at a native genomic locus encoding a SNAC polypeptide of the invention. By "native genomic locus" is intended a naturally occurring genomic sequence. The genomic locus may be modified to increase, reduce or eliminate the activity of the SNAC polypeptide. The term "genetically modified" as used herein refers to a plant or plant part that is modified in its genetic information by the introduction of one or more foreign polynucleotides, and the introduction of the foreign polynucleotide leads to a phenotypic change in the plant. By "phenotypic change" is intended a measurable change in one or more cell, tissue, or organ functions. For example, plants having a genetic modification at the genomic locus encoding a ZmSNAC polypeptide can show reduced or eliminated expression or activity of the NAC polypeptide. Various methods to generate such a genetically modified genomic locus are described elsewhere herein, as are the variety of phenotypes that can result from the modulation of the level and/or activity of one or more of the ZmSNAC sequences of the invention.

As used herein, the term plant includes reference to whole plants, plant parts or organs (e.g., leaves, stems, roots), plant cells and seeds and progeny of same. Plant cell, as used herein, includes, without limitation, cells obtained from or found in seeds, suspension cultures, embryos, meristematic regions, callus tissue, leaves, roots, shoots, gametophytes, sporophytes, pollen and microspores, as well as plant protoplasts and plant cell tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" refers to the mature seed produced by commercial growers for purposes other than growing or reproducing the species. Progeny, variants and mutants of the regenerated plants are also included within the scope of the invention, provided that these parts comprise the introduced nucleic acid sequences.

Methods

I. Providing Sequences

The sequences of the present invention can be introduced into and expressed in a host cell such as bacteria, yeast, insect, mammalian or optimally plant cells. It is expected that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli* or eukaryotic cells such as yeast, insect, amphibian or mammalian cells. Host cells can also be monocotyledonous or dicotyledonous plant cells. In certain embodiments, the monocotyledonous host cell is a maize host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures and the like.

The ZmSNAC polynucleotides of the invention can be provided in expression cassettes for expression in the plant of interest. The cassette will include 5' and 3' regulatory sequences operably linked to a ZmSNAC polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, "operably linked" means that the coding regions are in the same reading frame. The cassette may contain at least one additional gene to be cotransformed into the organism. Alternatively, the additional gene(s) can be provided on multiple expression cassettes. An expression cassette may be provided with a plurality of restriction sites and/or recombination sites for insertion of the ZmSNAC polynucleotide to be under the transcriptional regulation of the regulatory regions. The expression cassette may additionally contain selectable marker genes.

In certain embodiments, the expression cassette will include, in the 5'-3' direction of transcription, a transcriptional and translational initiation region, a ZmSNAC polynucleotide of the invention and a transcriptional and translational termination region functional in plants. The regulatory regions (i.e., promoters, transcriptional regulatory regions and translational termination regions) and/or the ZmSNAC polynucleotide of the invention may be native/analogous to the host cell or to each other. Alternatively, the regulatory regions and/or the ZmNAC polynucleotide of the invention may be heterologous to the host cell or to each other. As used herein with reference to a sequence, "heterologous" means a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus, or the promoter is not the native promoter for the operably-linked polynucleotide. As used herein, a chimeric gene comprises a coding sequence operably linked to a transcription initiation region that is heterologous to the coding sequence.

While heterologous promoters can be used to express the ZmSNAC sequences, the native promoter sequences or other NAC promoters may also be used. Such constructs can change expression levels of ZmSNAC sequences in the plant or plant cell. Thus, the phenotype of the plant or plant cell can be altered.

The termination region may be native with the transcriptional initiation region, may be native with the operably-linked ZmSNAC polynucleotide of interest, may be native with the plant host or may be derived from another source, i.e., foreign or heterologous with reference to the promoter, the ZmSNAC polynucleotide of interest, the plant host or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391 and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20) and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyan fluorescent protein (CYP) (Bolte, et al., (2004) *J. Cell Science* 117:943-54 and Kato, et al., (2002) *Plant Physiol* 129:913-42) and yellow fluorescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference. The above list of selectable marker genes is not meant to be limiting; any selectable marker gene can be used in the present invention.

Certain other marker genes for plant transformation require screening of presumptively transformed plant cells rather than direct genetic selection of transformed cells for resistance to a toxic substance such as an antibiotic. These marker genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, (1987) *Plant Mol. Biol. Rep.* 5:387 and U.S. Pat. No. 5,599,670; Teeri, et al.,(1989) *EMBO J.* 8:343, Koncz, et al., (1987) *Proc. Natl. Acad. Sci. U.S.A.* 84:131, De Block, et al., (1984) *EMBO J.* 3:1681. Another approach to the identification of relatively rare transformation events has been use of a gene that encodes a dominant constitutive regulator of the *Zea mays* anthocyanin pigmentation pathway. Ludwig, et al., (1990) *Science* 247: 449.

A number of promoters can be used in the practice of the invention, including the native promoter of a polynucleotide sequence of interest. The promoters can be selected based on the desired outcome. The nucleic acids can be combined with constitutive, inducible, tissue-preferred or other promoters for expression in plants.

Such constitutive promoters include, for example, the core promoter of the Rsyn7 promoter and other constitutive promoters disclosed in WO 99/43838 and U.S. Pat. No. 6,072, 050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), dMMV (double-enhanced version of the mirabilis mosaic virus promoter; see, Dey and Maiti, (1999) *Plant Molecular Biology* 40(5):771-782), LESVBV (enhanced strawberry vein banding virus promoter; see, US Patent Application Publication Number 2002/0182593) and the like. Other constitutive promoters include, for example, U.S. Pat. Nos. 5,608, 149; 5,608,144; 5,604,121; 5,569,597; 5,466,785; 5,399,680; 5,268,463; 5,608,142 and 6,177,611.

Tissue-preferred promoters can be utilized to target enhanced ZmNAC expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6): 1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression. See, also, US Patent Application Publication Number 2003/0074698, herein incorporated by reference.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:4732; Mitra, et al., (1994) *Plant Molecular Biology* 26:35-93; Kayaya, et al., (1995) *Molecular and General Genetics* 248:668-674 and Matsuoka, et al., (1993) *Proc. Natl. Acad. Sci. USA* 90(20):9586-9590. Senecence regulated promoters are also of use, such as, SAM22 (Crowell, et al., (1992) *Plant Mol. Biol.* 18:459-466). See, also, U.S. Pat. No. 5,689,042 herein incorporated by reference.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772); rolB promoter (Capana, et al., (1994) *Plant Mol. Biol.* 25(4):681-691 and the CRWAQ81 root-preferred promoter with the ADH first intron (US Patent Application Publication Number 2005/0097633). See also, U.S. Pat. Nos. 5,837,876; 5,750,386; 5,633,363; 5,459,252; 5,401,836; 5,110,732 and 5,023,179.

"Seed-preferred" promoters refers to those promoters active during seed development and may include expression in seed initials or related maternal tissue. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin and the like. For monocots, seed-specific promoters include, but are not limited to, maize 15 kDa zein, 22 kDa zein, 27 kDa zein, gamma-zein, waxy, shrunken 1 and shrunken 2. See also, WO 00/12733, where seed-preferred promoters from end1 and end2 genes are disclosed; herein incorporated by reference. Additional embryo specific promoters are disclosed in Sato, et al., (1996) *Proc. Natl. Acad. Sci.* 93:8117-8122; Nakase, et al., (1997) *Plant J* 12:235-46 and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 and Wu, et al., (1998) *Plant Cell Physiology* 39:885-889.

Also of interest are promoters active in meristem regions, such as developing inflorescence tissues and promoters which drive expression at or about the time of anthesis or early kernel development. This may include, for example, the maize Zag promoters, including Zag1 and Zag2 (see, Schmidt, et al., (1993) *The Plant Cell* 5:729-37; GenBank Accession Number X80206; Theissen, et al., (1995) *Gene* 156:155-166 and U.S. patent application Ser. No. 10/817, 483); maize Zap promoter (also known as ZmMADS; U.S. patent application Ser. No. 10/387,937; WO 03/078590); maize ckx1-2 promoter (US Patent Application Publication Number 2002/0152500 A1; WO 02/0078438); maize eep1 promoter (U.S. patent application Ser. No. 10/817,483); maize end2 promoter (U.S. Pat. No. 6,528,704 and U.S. patent application Ser. No. 10/310,191); maize lec1 promoter (U.S. patent application Ser. No. 09/718,754); maize F3.7 promoter (Baszczynski, et al., (1997) *Maydica* 42:189-201); maize tb1 promoter (Hubbarda, et al., (2002) *Genetics* 162: 1927-1935 and Wang, et al., (1999) *Nature* 398:236-239); maize eep2 promoter (U.S. patent application Ser. No. 10/817,483); maize thioredoxinH promoter (U.S. Provisional Patent Application Ser. No. 60/514,123); maize Zm40 promoter (U.S. Pat. No. 6,403,862 and WO 01/2178); maize mLIP15 promoter (U.S. Pat. No. 6,479,734); maize ESR promoter (U.S. patent application Ser. No. 10/786,679); maize PCNA2 promoter (U.S. patent application Ser. No. 10/388,359); maize cytokinin oxidase promoters (U.S. patent application Ser. No. 11/094,917); promoters disclosed in Weigal, et al., (1992) *Cell* 69:843-859; Accession Number AJ131822; Accession Number Z71981; Accession Number AF049870 and shoot-preferred promoters disclosed in McAvoy, et al., (2003) *Acta Hort. (ISHS)* 625:379-385. Other dividing cell or meristematic tissue-preferred promoters that may be of interest have been disclosed in Ito, et al., (1994) *Plant Mol. Biol.* 24:863-878; Regad, et al., (1995) *Mo. Gen. Genet.* 248:703-711; Shaul, et al., (1996) *Proc. Natl. Acad. Sci.* 93:4868-4872; Ito, et al., (1997) *Plant J.* 11:983-992 and Trehin, et al., (1997) *Plant Mol. Biol.* 35:667-672, all of which are hereby incorporated by reference herein.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani, et al., (1990) *Plant Mol Biol.* 15:605, Zm13 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721) and *B. napus* pollen specific genes (Arnoldo, et al., (1992) *J. Cell. Biochem, Abstract Number Y101204*).

Stress-inducible promoters include salt-inducible or water-stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57); osmotic inducible promoters, such as, Rab17 (Vilardell, et al., (1991) *Plant Mol. Biol.* 17:985-93) and osmotin (Raghothama, et al., (1993) *Plant Mol Biol* 23:1117-28) and heat inducible promoters, such as, heat shock proteins (Barros, et al., (1992) *Plant Mol.* 19:665-75; Marrs, et al., (1993) *Dev. Genet.* 14:27-41) and smHSP (Waters, et al., (1996) *J. Experimental Botany* 47:325-338). Other stress-inducible promoters include rip2 (U.S. Pat. No. 5,332,808 and US Patent Application Publication Number 2003/0217393), rab17 (Busk (1997) *Plant J* 11(6):1285-1295) and rd29a (Yamaguchi-Shinozaki, et al., (1993) *Mol. Gen. Genetics* 236:331-340). Manipulation of ZmNAC expression to improve abiotic stress tolerance may involve the use of tissue-preferred and/or stress-responsive promoters.

Stress-insensitive promoters can also be used in the methods of the invention. This class of promoters, as well as representative examples, are further described elsewhere herein.

Nitrogen-responsive promoters can also be used in the methods of the invention. Such promoters include, but are not limited to, the 22 kDa Zein promoter (Spena, et al., (1982) *EMBO J* 1:1589-1594 and Muller, et al., (1995) *J. Plant Physiol* 145:606-613); the 19 kDa zein promoter (Pedersen, et al., (1982) *Cell* 29:1019-1025); the 14 kDa zein promoter (Pedersen, et al., (1986) *J. Biol. Chem.* 261:6279-6284), the b-32 promoter (Lohmer, et al., (1991) *EMBO J* 10:617-624) and the nitrite reductase (NiR) promoter (Rastogi, et al., (1997) *Plant Mol Biol.* 34(3):465-76 and Sander, et al., (1995) *Plant Mol Biol.* 27(1):165-77). For a review of consensus sequences found in nitrogen-induced promoters, see for example, Muller, et al., (1997) *The Plant Journal* 12:281-291.

Chemically-regulated promoters can be used to modulate the expression of a gene in a plant through the application of an exogenous chemical regulator. Depending upon the objective, the promoter may be a chemically-inducible promoter, where application of the chemical induces gene expression or a chemical-repressible promoter, where application of the chemical represses gene expression. Chemically-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Additional inducible promoters include heat shock promoters, such as Gmhsp17.5-E (soybean) (Czarnecka, et al., (1989) *Mol Cell Biol.* 9(8):3457-3463); APX1 gene promoter (*Arabidopsis*) (Storozhenko, et al., (1998) *Plant Physiol.* 118 (3):1005-1014): Ha hsp17.7 G4 (*Helianthus annuus*) (Almoguera, et al., (2002) *Plant Physiol.* 129(1):333-341 and Maize Hsp70 (Rochester, et al., (1986) *EMBO J.* 5: 451-8.)

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides or polypeptides into plants are known in the art and include, but are not limited to, stable transformation methods, transient transformation methods and virus-mediated methods. "Stable transformation" is intended to mean that the introduced nucleotide construct integrates into the genome of the plant and is capable of being inherited by the progeny thereof. "Transient transformation" is intended to mean that a sequence is introduced into the plant but is only temporarily expressed or present in the plant.

Transformation protocols, as well as protocols for introducing polypeptides or polynucleotide sequences into plants, may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. No. 5,563,055 and U.S. Pat. No. 5,981,840), direct gene transfer (Paszkowski, et al., (1984) *EMBO J.* 3:2717-2722) and ballistic particle acceleration (see, for example, U.S. Pat. No. 4,945,050; U.S. Pat. No. 5,879,918; U.S. Pat. Nos. 5,886,244 and 5,932,782; Tomes, et al., (1995) in *Plant Cell, Tissue, and Organ Culture: Fundamental Methods*, ed. Gamborg and Phillips, (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Hoque, et al., (2005) *Plant Cell Tissue & Organ Culture* 82(1):45-55 (rice); Sreekala, et al., (2005) *Plant Cell Reports* 24(2):86-94 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311: 763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*), all of which are herein incorporated by reference.

In specific embodiments, the ZmSNAC sequences of the invention can be provided to a plant using a variety of transient transformation methods. Such transient transformation methods include, but are not limited to, the introduction of the ZmSNAC protein or variants and fragments thereof directly into the plant or the introduction of a ZmSNAC transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the ZmSNAC polynucleotide can be transiently transformed into the plant using other techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethyleneimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that a ZmSNAC polynucleotide of the invention may be initially synthesized as part of a viral polyprotein, which later may be processed by proteolysis in vivo or in vitro to produce the desired recombinant protein. Further, it is recognized that promoters useful for the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931 and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, and U.S. Pat. Nos. 6,187,994; 6,552,248; 6,624,297; 6,331, 661; 6,262,341; 6,541,231; 6,664,108; 6,300,545; 6,528,700 and 6,911,575, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional means. See, for example, McCormick, et al., (1986) *Plant Cell Reports* 5:81-84. These plants may then be pollinated with either the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved. In this manner, the present invention provides transformed seed (also referred to as "transgenic seed") having a polynucleotide of the invention, for example, an expression cassette of the invention, stably incorporated into its genome.

Pedigree breeding starts with the crossing of two genotypes, such as an elite line of interest and one other inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F$_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. Backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of a maize inbred line of interest, comprising the steps of crossing a plant of a maize inbred line of interest with a donor plant comprising a mutant gene or transgene conferring a desired trait (i.e., a modulation in the expression of a ZmSNAC polynucleotide, or any plant phenotype resulting from the modulated ZmSNAC expression level such as those phenotypes discussed elsewhere herein, including improved abiotic stress tolerance); selecting an F1 progeny plant comprising the mutant gene or transgene conferring the desired trait and backcrossing the selected F1 progeny plant to a plant of the maize inbred line of interest. This method may further comprise the step of obtaining a molecular marker profile of the maize inbred line of interest and using the molecular marker profile to select for a progeny plant with the desired trait and the molecular marker profile of the inbred line of interest. In the same manner, this method may be used to produce F1 hybrid seed by adding a final step of crossing the desired trait conversion of the maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14) or ultraviolet radiation (preferably from 2500 to 2900 nm) or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid or acridines. Once a desired trait is observed through mutagenesis the trait may then be incorporated into existing germplasm by traditional breeding techniques, such as backcrossing. Details of mutation breeding can be found in "Principals of Cultivar Development," Fehr, 1993 Macmillan Publishing Company, the disclosure of which is incorporated herein by reference. In addition, mutations created in other lines may be used to produce a backcross conversion of elite lines that comprises such mutations.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals and conifers.

Vegetables include tomatoes (*Lycopersicon esculentum*), lettuce (e.g., *Lactuca sativa*), green beans (*Phaseolus vul-* garis), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal and in yet other embodiments corn plants are optimal.

Other plants of interest include grain plants that provide seeds of interest, oil-seed plants and leguminous plants. Seeds of interest include grain seeds, such as maize, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired. A protein of the present invention, once expressed, can be isolated from yeast by lysing the cells and applying standard protein isolation techniques to the lists. The monitoring of the purification process can be accomplished by using Western blot techniques or radioimmunoassay or other standard immunoassay techniques.

The sequences of the present invention can also be ligated to various expression vectors for use in transfecting cell cultures of, for instance, mammalian, insect or plant origin. As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213-238).

II. Modulating the Level and/or Activity of a ZmSNAC Polypeptide

A method for modulating the level and/or activity of the polypeptide of the present invention in a plant is provided. In general, the level and/or activity of the ZmSNAC polypeptide is increased or reduced by at least 1%, 5%, 10%, 20%, 30%, 40%, 50%, 60%, 70%, 80% or 90% or more, relative to a native control plant, plant part or cell which does not comprise the introduced sequence. Modulation of the level and/or activity may occur at one or more stages of development. In specific embodiments, the polypeptides of the present invention are modulated in monocots, such as maize.

The expression level of the ZmSNAC polypeptide may be measured directly, for example, by assaying for the level of the ZmSNAC polypeptide in the plant, or indirectly, for example by measuring DNA binding activity and/or transgenic activation of gene expression in vitro or in vivo.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984, all of which are herein incorporated by reference. See also, WO 98/49350, WO 99/07865, WO 99/25821 and Beetham, et al., (1999) *Proc. Natl. Acad. Sci. USA* 96:8774-8778, herein incorporated by reference.

It is therefore recognized that methods of the present invention do not depend on the incorporation of the entire polynucleotide into the genome, only that the plant or cell is altered as a result of the introduction of the polynucleotide into a cell. In one embodiment of the invention, the genome may be altered following the introduction of a polynucleotide into a cell. For example, the polynucleotide, or any part thereof, may incorporate into the genome of the plant. Alterations to the genome include, but are not limited to, additions, deletions and substitutions of nucleotides into the genome. While the methods of the present invention do not depend on additions, deletions and substitutions of any particular number of nucleotides, it is recognized that such additions, deletions or substitutions comprise at least one nucleotide.

It is further recognized that modulating the level and/or activity of the ZmSNAC sequence can be manipulated so as to occur only during certain developmental stages. Control of ZmSNAC expression can be obtained via the use of inducible promoters, tissue-preferred promoters or promoters active exclusively or preferentially at one or more developmental stages. Alternatively, the gene could be inverted or deleted using site-specific recombinases, transposons or recombination systems.

A "subject plant or plant cell" is one in which genetic alteration, such as transformation, has been affected as to a gene of interest or is a plant or plant cell which is descended from a plant or cell so altered and which comprises the alteration. A "control" or "control plant" or "control cell" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

In the present case, for example, changes in ZmSNAC transcription factor levels or activity could be measured by comparing performance of a subject plant or plant cell to a control plant or plant cell under drought or other abiotic stress conditions. In addition, changes in gene expression induced by ZmSNAC modulation could be assayed using gene-expression profiling technologies.

In certain embodiments the nucleic acid constructs of the present invention can be used in combination ("stacked") with other polynucleotide sequences of interest in order to create plants with a desired phenotype. The polynucleotides of the present invention may be stacked with any gene or combination of genes and the combinations generated can include multiple copies of any one or more of the polynucleotides of interest. The desired combination may affect one or more traits; for example, the constructs and methods of the invention could be used in combination with other genes that confer tolerance to drought or other abiotic stresses, such as salt or heat stress, as well as with genes designed to enhance yield. Other combinations may be designed to produce plants with a variety of desired traits, such as those described elsewhere herein.

A. Increasing the Activity and/or Level of a ZmSNAC Polypeptide

Methods are provided to increase the activity and/or level of a ZmSNAC polypeptide of the invention. An increase in the level of concentration and/or activity of a ZmSNAC polypeptide of the invention can be achieved by providing to the plant a ZmSNAC polypeptide. As discussed elsewhere herein, many methods are known in the art for providing a polypeptide to a plant including, but not limited to, direct introduction of the polypeptide into the plant, and introducing into the plant (transiently or stably) a polynucleotide construct encoding a polypeptide having SNAC transcription factor activity. Thus, the level and/or activity of a ZmSNAC polypeptide may be increased by altering the gene encoding the ZmSNAC polypeptide or its promoter. It is also recognized that the methods of the invention may employ a polynucleotide that is not capable of directing, in the transformed plant, the expression of a protein or RNA. See, e.g., Kmiec, U.S. Pat. No. 5,565,350; Zarling, et al., PCT/US93/03868. Plants are provided which carry mutations affecting one or more ZmSNAC genes, wherein the mutations increase expression of at least one ZmSNAC gene or increase the level or activity of at least one encoded ZmSNAC polypeptide. As described elsewhere herein, methods to assay for an increase in level or activity of a ZmSNAC polypeptide are known.

B. Reducing the Activity and/or Level of a ZmNAC Polypeptide

Methods are provided to reduce or eliminate the activity and/or level (concentration) of a ZmSNAC polypeptide by transforming a plant cell with an expression cassette that expresses a polynucleotide that inhibits the expression of the ZmSNAC polypeptide. The polynucleotide may inhibit the expression of a ZmSNAC polypeptide directly, by preventing translation of the ZmSNAC polypeptide messenger RNA, or indirectly, by encoding a molecule that inhibits the transcription or translation of a gene encoding a ZmSNAC polypeptide. Methods for inhibiting or eliminating the expression of a gene in a plant are well known in the art, and any such method may be used in the present invention to inhibit the expression of the ZmSNAC polypeptides.

In accordance with the present invention, the expression of a ZmSNAC polypeptide is inhibited if the level of the ZmSNAC polypeptide is statistically lower than the level of the same ZmSNAC polypeptide in a plant that has not been genetically modified to inhibit the expression of that ZmSNAC polypeptide. In particular embodiments of the invention, the level or activity of the ZmSNAC polypeptide in a modified plant according to the invention is less than 95%, less than 90%, less than 80%, less than 70%, less than 60%, less than 50%, less than 40%, less than 30%, less than 20%, less than 10% or less than 5% of the level or activity of the same ZmSNAC polypeptide in a control plant. The expression level of the ZmSNAC polypeptide may be measured directly, for example, by assaying for the level of the ZmSNAC polypeptide expressed in the cell or plant, or indirectly, for example, by measuring DNA binding activity or protein interaction in the cell or plant.

In other embodiments of the invention, the activity of one or more ZmSNAC polypeptides is reduced or eliminated by transforming a plant cell with an expression cassette comprising a polynucleotide encoding a polypeptide that inhibits the activity of one or more ZmSNAC polypeptides. The activity of a ZmSNAC polypeptide is inhibited according to the present invention if the transcription factor activity of the ZmSNAC polypeptide is statistically lower than the corresponding activity of the same ZmSNAC polypeptide in a control plant or cell. In particular embodiments of the invention, the activity of the ZmSNAC polypeptide in a modified plant according to the invention is less than 95%, less than 90%, less than 80%, less than 70%, less than 60%, less than 50%, less than 40%, less than 30%, less than 20%, less than 10% or less than 5% of the activity of the same ZmSNAC polypeptide in a control plant or cell. The activity of a ZmSNAC polypeptide is "eliminated" according to the invention when it is not detectable by the assay methods described elsewhere herein.

In other embodiments, the activity of a ZmSNAC polypeptide may be reduced or eliminated by disrupting the gene encoding the ZmSNAC polypeptide. The invention encompasses mutagenized plants that carry mutations in ZmSNAC genes, where the mutations reduce expression of the ZmSNAC gene or inhibit the activity of the encoded ZmSNAC polypeptide.

Thus, many methods may be used to reduce or eliminate the activity of a ZmSNAC polypeptide. More than one method may be used to reduce the activity of a single ZmSNAC polypeptide. In addition, combinations of methods may be employed to reduce or eliminate the activity of two or more different ZmSNAC polypeptides.

Non-limiting examples of methods of reducing or eliminating the expression of a ZmSNAC polypeptide are given below.

1. Polynucleotide-Based Methods

In some embodiments of the present invention, a plant cell is transformed with an expression cassette that is capable of expressing a polynucleotide that inhibits the expression of a ZmSNAC sequence. The term "expression" as used herein refers to the biosynthesis of a gene product, including the transcription and/or translation of said gene product. For example, for the purposes of the present invention, an expression cassette capable of expressing a polynucleotide that inhibits the expression of at least one ZmSNAC sequence is an expression cassette capable of producing an RNA molecule that inhibits the transcription and/or translation of at least one ZmSNAC polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a ZmSNAC sequence are given below.

i. Sense Suppression/Cosuppression

In some embodiments of the invention, inhibition of the expression of a ZmSNAC polypeptide may be obtained by sense suppression or cosuppression. For cosuppression, an expression cassette is designed to express an RNA molecule corresponding to all or part of a messenger RNA encoding a ZmSNAC polypeptide in the "sense" orientation. Over expression of the RNA molecule can result in reduced expression of the native gene. Accordingly, multiple plant lines transformed with the cosuppression expression cassette are screened to identify those that show the greatest inhibition of ZmSNAC polypeptide expression.

The polynucleotide used for cosuppression may correspond to all or part of the sequence encoding the ZmSNAC polypeptide, all or part of the 5' and/or 3' untranslated region of a ZmSNAC polypeptide transcript or all or part of both the coding sequence and the untranslated regions of a transcript encoding a ZmSNAC polypeptide. In some embodiments where the polynucleotide comprises all or part of the coding region for the ZmSNAC polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the invention, inhibition of the expression of the ZmSNAC polypeptide may be obtained by antisense suppression. For antisense suppression, the expression cassette is designed to express an RNA molecule complementary to all or part of a messenger RNA encoding the ZmSNAC polypeptide. Overexpression of the antisense RNA molecule can result in reduced expression of the native gene. Accordingly, multiple plant lines transformed with the antisense suppression expression cassette are screened to identify those that show the desired inhibition of ZmSNAC polypeptide expression.

The polynucleotide for use in antisense suppression may correspond to all or part of the complement of the sequence encoding the ZmSNAC polypeptide, all or part of the complement of the 5' and/or 3' untranslated region of the ZmSNAC polypeptide transcript or all or part of the complement of both the coding sequence and the untranslated regions of a transcript encoding the ZmSNAC polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of a ZmSNAC polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the desired level of inhibition of ZmSNAC polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631 and WO 00/49035; each of which is herein incorporated by reference.

iv. Hairpin RNA Interference and Intron-Containing Hairpin RNA Interference

In some embodiments of the invention, inhibition of the expression of one or more ZmSNAC polypeptides may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoded by the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

Alternatively, the base-paired stem region may correspond to a portion of a promoter sequence controlling expression of the gene to be inhibited. Transcriptional gene silencing (TGS) may be accomplished through use of hpRNA constructs wherein the inverted repeat of the hairpin shares sequence identity with the promoter region driving expression of a gene to be silenced. See, for example, US Patent Application Publication 2005/0246796. Processing of the hpRNA into short RNAs which can interact with the homologous promoter region may trigger degradation or methylation to result in silencing (Aufsatz, et al., (2002) *PNAS* 99(4):16499-16506; Mette, et al., (2000) *EMBO J* 19(19):5194-5201). In other embodiments, the hairpin inverted repeat is based on and homologous to, the 3' untranslated region of the gene to be inhibited.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for ZmSNAC polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,635,805, each of which is herein incorporated by reference.

vi. Ribozymes

In some embodiments, the polynucleotide expressed by the expression cassette of the invention is catalytic RNA or has ribozyme activity specific for the messenger RNA of a ZmSNAC polypeptide. Thus, the polynucleotide causes the degradation of the endogenous messenger RNA, resulting in reduced expression of the ZmSNAC polypeptide. This method is described, for example, in U.S. Pat. No. 4,987,071, herein incorporated by reference.

vii. Small Interfering RNA or Micro RNA

In some embodiments of the invention, inhibition of the expression of one or more ZmSNAC polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ZmSNAC polypeptide expression, the 22-nucleotide sequence is selected from a ZmSNAC polypeptide transcript sequence and contains 22 nucleotides encoding said ZmSNAC polypeptide sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding a ZmSNAC polypeptide, resulting in reduced expression of the gene. In particular embodiments, the zinc finger protein binds to a regulatory region of a ZmSNAC polypeptide gene. In other embodiments, the zinc finger protein binds to a messenger RNA encoding a ZmSNAC polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355; each of which is herein incorporated by reference.

3. Polypeptide-Based Inhibition of Protein Activity

In some embodiments of the invention, the polynucleotide encodes an antibody that binds to at least one ZmSNAC polypeptide and reduces the activity of the ZmSNAC polypeptide. In another embodiment, the binding of the antibody results in increased turnover of the antibody-ZmSNAC polypeptide complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a ZmSNAC polypeptide is reduced or eliminated by disrupting the gene encoding the ZmSNAC polypeptide. The gene encoding the ZmSNAC polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced ZmSNAC activity. ZmSNAC down-regulated plants could be assayed for a decrease in expression of either ZmSNAC itself or of genes regulated by it. In addition, downregulation of ZmSNAC should have a measureable phenotype related to drought and yield.

i. Transposon Tagging

In one embodiment of the invention, the expression of one or more ZmSNAC polypeptides is reduced or eliminated by inserting a transposon within a regulatory region or coding region of the gene encoding the ZmSNAC polypeptide. A transposon may be inserted within an exon, intron, 5' or 3' untranslated sequence, a promoter or any other regulatory sequence of a ZmSNAC polynucleotide. Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see Ohshima, et al., (1998) *Virology* 243: 472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products, is also applicable to the instant invention. See, McCallum, et al., (2000) *Nat. Biotechnol.* 18:455-457, herein incorporated by reference.

Mutations that impact gene expression or that interfere with the function of the encoded protein are well known in the art. Insertional mutations in gene exons usually result in null mutants. Mutations in conserved residues are particularly effective in inhibiting the activity of the encoded protein. Conserved residues of NAC polypeptides have been described (Ernst, et al., (2004) *EMBO Reports* 5(3):297-303) and provide a basis for designing mutations with the goal of eliminating the ZmSNAC transcription factor activity. See, for example, FIG. 1. Such mutants can be isolated according to well-known procedures, and mutations in different ZmSNAC loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more ZmSNAC polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778; each of which is herein incorporated by reference.

III. Modulating ZmSNAC Transcription Factor Level and/or Activity

"Modulating ZmSNAC transcription factor level and/or activity" includes any statistically significant decrease or increase in level and/or activity of said factor in the plant when compared to a control plant. The modulated level and/or activity of the ZmSNAC transcription factor can comprise either an increase or a decrease of about 0.1%, 0.5%, 1%, 5%, 10%, 15%, 20%, 25%, 30%, 35%, 40%, 45%, 50%, 55%, 60%, 65%, 70%, 75%, 80%, 85%, 90%, 95% or more when compared to a control. It is further recognized that the modulation of the ZmSNAC level/activity need not be an overall increase/decrease in ZmSNAC level and/or activity, but may comprise a change in tissue distribution of the transcription factor activity. Moreover, the modulation of the transcription factor level/activity need not be an overall increase/decrease, but also includes a change in the ratio of activity of various transcription factors.

Methods for assaying a modulation in transcription factor level and/or activity are known in the art. As discussed elsewhere herein, modulation in ZmSNAC level and/or activity can further be detected by monitoring for particular plant phenotypes. Because ZmSNAC genes regulate the expression of other genes, modulation of a ZmSNAC gene should be measurable by changes in target gene expression.

In specific methods, the level and/or activity of a ZmSNAC transcription factor in a plant is increased by increasing the level or activity of the ZmSNAC polypeptide in the plant. Methods for increasing the level and/or activity of ZmSNAC polypeptides in a plant are discussed elsewhere herein. In certain embodiments, a ZmSNAC nucleotide sequence encoding a ZmSNAC polypeptide can be provided by introducing into the plant a polynucleotide comprising a ZmSNAC nucleotide sequence of the invention, expressing the ZmSNAC sequence and thereby increasing the level and/or activity of said transcription factor in the plant or plant part when compared to a control. In some embodiments, the ZmSNAC nucleotide construct introduced into the plant is stably incorporated into the genome of the plant.

In other methods, the level and/or activity of ZmSNAC transcription factors in a plant is decreased by decreasing the level and/or activity of one or more of the ZmSNAC polypeptides in the plant. Such methods are disclosed in detail elsewhere herein. In one such method, a ZmSNAC nucleotide sequence is introduced into the plant and expression of the ZmSNAC nucleotide sequence decreases the level and/or activity of the ZmSNAC polypeptide in the plant or plant part when compared to a control plant or plant part. In certain embodiments, the nucleotide construct introduced into the plant is stably incorporated into the genome of the plant.

As discussed above, one of skill will recognize the appropriate promoter to use to modulate the level/activity of a ZmSNAC transcription factor in the plant. Exemplary promoters for this embodiment have been disclosed elsewhere herein.

Accordingly, the present invention further provides plants having a modulated level/activity of a ZmSNAC transcription factor when compared to said level/activity in a control plant. In one embodiment, the plant of the invention has an increased level/activity of the ZmSNAC polypeptide of the invention. In other embodiments, the plant of the invention has a reduced or eliminated level of the ZmSNAC polypeptide of the invention. In certain embodiments, such plants have stably incorporated into their genome a nucleic acid molecule comprising a ZmSNAC nucleotide sequence of the invention operably linked to a promoter that drives expression in the plant cell.

A. Modulating Root Development

Modulation of the level/activity of a ZmSNAC transcription factor may result in modulated root development when compared to a control plant. Such alterations in root development include, but are not limited to, alterations in the size or growth rate of the primary root, the fresh root weight, the extent of lateral and adventitious root formation, the vasculature system, meristem development and radial expansion. Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Modulated root development may also impact the standability of a plant. The term "resistance to lodging" or "standability" refers to the ability of a plant to fix itself to the soil. For plants with an erect or semi-erect growth habit, this term also refers to the ability to maintain an upright position under adverse environmental conditions. This trait relates to the size, depth and morphology of the root system. In addition, stimulating root growth and increasing root mass at appropriate developmental stages also finds use in promoting in vitro propagation of explants.

Increased root biomass and/or altered root architecture may also find use in improving nitrogen-use efficiency of the plant. Such improved efficiency may lead to, for example, an increase in plant biomass and/or seed yield at an existing level of available nitrogen or maintenance of plant biomass and/or seed yield when available nitrogen is limited. Thus, agronomic and/or environmental benefits may ensue.

Furthermore, higher root biomass production has an indirect effect on production of compounds produced by root cells or transgenic root cells or cell cultures of said transgenic root cells. One example of an interesting compound produced in root cultures is shikonin, the yield of which can be advantageously enhanced by said methods.

B. Modulating Shoot and Leaf Development

Methods are also provided for modulating vegetative tissue growth in plants. In one embodiment, shoot and/or leaf development in a plant is modulated when compared to a control plant or plant part. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a ZmSNAC polypeptide of the invention. In one embodiment, a ZmSNAC sequence of the invention is provided. In other embodiments, the ZmSNAC nucleotide sequence can be provided by introducing into the plant a polynucleotide comprising a ZmSNAC nucleotide sequence of the invention, expressing the ZmSNAC sequence, and thereby modifying shoot and/or leaf development. In certain embodiments, the ZmSNAC nucleotide construct introduced into the plant is stably incorporated into the genome of the plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, senescence-activated promoters, stress-induced promoters, nitrogen-induced promoters and leaf-preferred promoters. Exemplary promoters have been disclosed elsewhere herein.

Decreasing ZmSNAC activity in a plant generally results in shorter internodes and stunted growth. Thus, the methods of the invention find use in producing dwarf plants. In addition, as discussed above, modulation of ZmSNAC activity in the plant may modulate both root and shoot growth. Thus, the present invention further provides methods for altering the root/shoot ratio.

It is further recognized that increasing seed size and/or weight can be accompanied by an increase in the rate of growth of seedlings or an increase in vigor. In addition, modulating the plant's tolerance to stress, as discussed elsewhere herein, along with modulation of root, shoot and leaf development, can increase plant yield and vigor. As used herein, the term "vigor" refers to the relative health, productivity, and rate of growth of the plant and/or of certain plant parts, and may be reflected in various developmental attributes, including, but not limited to, concentration of chlorophyll, photosynthetic rate, total biomass, root biomass, grain quality and/or grain yield. In *Zea mays* in particular, vigor may also be reflected in ear growth rate, ear size and/or rate or degree of silk exsertion. Vigor may relate to the ability of a plant to grow rapidly during early development and to the successful establishment of a well-developed root system and a well-developed photosynthetic apparatus. Vigor may be determined with reference to different genotypes under similar environmental conditions, or with reference to the same or different genotypes under different environmental conditions.

Accordingly, the present invention further provides plants having modulated shoot and/or leaf development when compared to a control plant. In some embodiments, the plant of the invention has an increased level/activity of a ZmSNAC polypeptide of the invention. In other embodiments, the plant of the invention has a decreased level/activity of the ZmSNAC polypeptide of the invention.

C. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant or plant part. "Modulating floral development" further includes any alteration in the timing of the development of a plant's reproductive tissue (i.e., delayed or accelerated floral development) when compared to a control plant or plant part. Macroscopic alterations may include changes in size, shape, number or location of reproductive organs, the developmental time period during which these structures form or the ability to maintain or proceed through the flowering process in times of environmental stress. Microscopic alterations may include changes to the types or shapes of cells that make up the reproductive organs.

The method for modulating floral development in a plant comprises modulating (either increasing or decreasing) the level and/or activity of the ZmSNAC polypeptide in a plant. In one method, a ZmSNAC sequence of the invention is provided. A ZmSNAC nucleotide sequence can be provided by introducing into the plant a polynucleotide comprising a ZmSNAC nucleotide sequence of the invention, expressing the ZmSNAC sequence, and thereby modifying floral development. In some embodiments, the ZmSNAC nucleotide construct introduced into the plant is stably incorporated into the genome of the plant.

As discussed above, one of skill will recognize the appropriate promoter to use to modulate floral development in the plant. Exemplary promoters for this embodiment include constitutive promoters, inducible promoters, shoot-preferred promoters and inflorescence-preferred promoters (including developing-female-inflorescence-preferred promoters), including those listed elsewhere herein.

Accordingly, the present invention further provides plants having modulated floral development when compared to the floral development of a control plant. Compositions include plants with a modulated level/activity of one or more ZmSNAC polypeptides of the invention and having an altered floral development, which may include the capacity to sustain normal reproductive development under abiotic stress conditions.

D. Modulating the Stress Tolerance of a Plant

Methods are provided for the use of the ZmSNAC sequences of the invention to modify the tolerance of a plant to abiotic stress. Promoters that can be used in this method are described elsewhere herein, including low-level constitutive, stress-insensitive or inducible, particularly stress-inducible, promoters. Accordingly, in one method of the invention, a plant's tolerance to stress is increased or maintained when compared to a control plant by introducing into the plant a polynucleotide comprising a ZmSNAC nucleotide sequence of the invention, expressing the ZmSNAC sequence, and thereby increasing the plant's tolerance to stress. In certain embodiments, the ZmSNAC nucleotide construct introduced into the plant is stably incorporated into the genome of the plant.

Increased growth of seedlings or early vigor is often associated with an increase in stress tolerance. For example, faster development of seedlings, including the root system of seedlings upon germination, is critical for survival, particularly under adverse conditions such as drought.

Methods are also provided to increase or maintain seed set during abiotic stress episodes. During periods of stress (i.e., drought, salt, heavy metals, temperature, etc.) embryo development is often aborted. In maize, halted embryo development results in aborted kernels on the ear (Cheikh and Jones, (1994) *Plant Physiol.* 106:45-51; Dietrich, et al., (1995) *Plant Physiol Biochem* 33:327-336). In soy, abortion of pods prior to seed maturation can reduce seed yield and is observed during both optimal and stress conditions. Preventing this seed loss will maintain yield. Accordingly, methods are provided to increase the stress resistance in a plant (e.g., during flowering and seed development). Increasing expression of the ZmSNAC sequence of the invention can modulate floral development during periods of stress, and thus methods are provided to maintain or improve the flowering process in plants under stress. The method comprises increasing the level and/or activity of one or more of the ZmSNAC sequences of the invention. In one method, a ZmSNAC nucleotide sequence is introduced into the plant and the level and/or activity of the ZmSNAC polypeptide is increased, thereby maintaining or improving the tolerance of the plant under stress conditions. In certain methods, the ZmSNAC nucleotide construct introduced into the plant is stably incorporated into the genome of the plant.

Significant yield instability can occur as a result of unfavorable environments during the lag phase of seed development. During this period, seeds undergo dramatic changes in ultra structure, biochemistry, and sensitivity to environmental perturbation, yet demonstrate little change in dry mass accumulation. Two important events that occur during the lag phase are initiation and division of endosperm cells and amyloplasts (which are the sites for starch deposition). In crop species such as maize, kernel sink capacity is principally a function of the number of endosperm cells and starch granules established during the first 6 to 12 days after pollination. The final number of endosperm cells and amyloplasts formed is highly correlated with final kernel weight. (Capitanio, et al., (1983); Reddy and Daynard, (1983); Jones, et al., (1985) (1996); Engelen-Eigles, et al., (2000)).

In this embodiment, a variety of promoters could be used to direct the expression of a sequence capable of increasing the level and/or activity of the ZmSNAC polypeptide, including but not limited to, constitutive promoters, seed-preferred promoters, developing-seed promoters, meristem-preferred promoters, stress-induced promoters and inflorescence-preferred (such as developing female inflorescence promoters). In one method, a promoter that is stress-inducible and is expressed in a tissue of the developing seed during the lag phase of development is used. By "lag phase" promoter is intended a promoter that is active in the lag phase of seed development. A description of this developmental phase is found elsewhere herein. By "developing-seed-preferred" is intended a promoter that allows for enhanced ZmSNAC expression within a developing seed. Such promoters that are stress insensitive and are expressed in a tissue of the developing seed during the lag phase of development are known in the art and include Zag2.1 (Theissen, et al., (1995) Gene 156:155-166, Genbank Accession Number X80206), and mzE40 (Zm40) (U.S. Pat. No. 6,403,862 and WO01/2178).

Methods to assay for an increase in seed set during abiotic stress are known in the art. For example, plants having the increased ZmSNAC activity can be monitored under various stress conditions and compared to control plants. For instance, the plant having the increased ZmSNAC transcription factor activity can be subjected to various degrees of stress during flowering and seed set. Under identical conditions, the genetically modified plant having the increased ZmSNAC transcription factor activity will have a higher number of developing pods and/or seeds than a control plant.

Accordingly, the present invention further provides plants having increased yield or a maintained yield and/or an increased or maintained flowering process during periods of abiotic stress (for example, drought, salt, heavy metals, temperature extremes). In some embodiments, the plants having an increased or maintained yield during abiotic stress have an increased level/activity of the ZmSNAC polypeptide of the invention. In some embodiments, the plant comprises a ZmSNAC nucleotide sequence of the invention operably linked to a promoter that drives expression in the plant cell. In some embodiments, such plants have stably incorporated into their genome a nucleic acid molecule comprising a ZmSNAC nucleotide sequence of the invention operably linked to a promoter that drives expression in the plant cell.

IV. Antibody Creation and Use

Antibodies can be raised to a protein of the present invention, including variants and fragments thereof, in both their naturally-occurring and recombinant forms. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature,* 277:491-492; Wolfenden, et al., (1981) *Biochemistry* 208:49-855; Kyte and Doolite, (1982) *J. Mol Biol.* 157:105-132; Rose, et al., (1985) *Science* 229:834-838. The antibodies can be used to screen expression libraries for particular expression products such as normal or abnormal protein or altered levels of the same, which may be useful for detecting or diagnosing various conditions related to the presence of the respective antigens. Assays indicating high levels of a ZmSNAC protein of the invention, for example, could be useful in detecting plants, or specific plant parts, with elevated ZmSNAC transcription factor levels. Usually the antibodies in such a procedure are labeled with a moiety which allows easy detection of presence of antigen/antibody binding.

The ZmSNAC1 regulatory element will be operably linked to a sequence of interest, which will provide for modification of the phenotype of the plant. Such modification includes modulating the production of an endogenous product, as to amount, relative distribution, or the like, or for providing a novel function or expression product. For example, such a promoter is useful for modulation of expression of sequences encoding stress-responsive proteins, including other transcription factors. Additionally, linking a stress-induced promoter with a marker, and, in particular, a visual marker, may be useful in tracking the expression of a linked gene of interest. Commonly used genes for screening presumptively transformed cells include β-glucuronidase (GUS), β-galactosidase, luciferase and chloramphenicol acetyltransferase. Jefferson, (1987) *Plant Mol. Biol. Rep.* 5:387 and U.S. Pat. No. 5,599,670; Teeri, et al., (1989) *EMBO J.* 8:343, Koncz, et al., (1987) *Proc. Natl. Acad. Sci. U.S.A.* 84:131, De Block, et al., (1984) *EMBO J.* 3:1681. Another approach to the identification of relatively rare transformation events has been use of a gene that encodes a dominant constitutive regulator of the *Zea mays* anthocyanin pigmentation pathway. Ludwig, et al., (1990) *Science* 247:449.

A method for expressing an isolated nucleotide sequence in a plant using the regulatory sequences disclosed herein is provided. The method comprises transforming a plant cell with a transformation vector that comprises an isolated nucleotide sequence operably linked to a plant regulatory sequence of the present invention and regenerating a stably transformed plant from the transformed plant cell. In this manner, the regulatory sequences are useful for controlling the expression of endogenous as well as exogenous products in a stress-induced manner.

Frequently it is desirable to have preferential expression of a DNA sequence in a tissue of an organism, or under certain environmental conditions. For example, increased resistance of a plant to insect attack might be accomplished by genetic manipulation of the plant's genome to comprise a tissue-specific promoter operably linked to a heterologous insecticide gene such that the insect-deterring substances are specifically expressed in the susceptible plant tissues. Increased tolerance to abiotic stress might be accomplished by genetic manipulation of the plant's genome to comprise a stress-induced promoter operably linked to a heterologous gene encoding a biosynthetic or regulatory gene for a plant hormone such that the hormone is specifically synthesized or its synthesis is regulated under the stress conditions. Preferential expression of the heterologous nucleotide sequence in the appropriate tissue or under the appropriate conditions reduces the drain on the plant's resources that occurs when a constitutive promoter initiates transcription of a heterologous nucleotide sequence throughout the cells of the plant and/or under all conditions.

Alternatively, it might be desirable to inhibit expression of a native DNA sequence within a plant's tissues to achieve a desired phenotype. For example, a hairpin configuration comprising all or a portion of a ZmSNAC1 promoter may be used to downregulate the native stress-responsive ZmSNAC1.

By "regulatory element" is intended sequences responsible for expression of the associated coding sequence including, but not limited to, promoters, terminators, enhancers, introns and the like.

By "terminator" is intended a regulatory region of DNA that causes RNA polymerase to disassociate from DNA, causing termination of transcription.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomal binding sites, transcriptional start and stop sequences, translational start and stop sequences, activator sequence and the like.

In the same manner, the promoter elements which enable expression under stress conditions can be identified, isolated, and used with other core promoters. By core promoter is meant the minimal sequence required to initiate transcription, such as the sequence called the TATA box which is common to promoters in genes encoding proteins. Thus the upstream promoter of ZmSNAC1 can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive stress-induced expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. The term "isolated" refers to material, such as a nucleic acid or protein, (1) which is substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art.

The *Zea mays* SNAC1 promoter is set forth in SEQ ID NO: 11 and is 1625 nucleotides in length.

The promoter regions from genes homologous to ZmSNAC1 may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals and conifers. Preferably, plants include corn, soybean, sunflower, safflower, canola, wheat, barley, rye, alfalfa and sorghum.

Promoter sequences from other plants may be isolated according to well-known techniques based on sequence homology. In these techniques, all or part of the known coding sequence is used as a probe which selectively hybridizes to other sequences present in a population of cloned genomic DNA fragments (i.e., genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions and which drive expression of an operably-linked sequence under conditions similar to those under which the native promoter is active. Functional variants of the invention may be created by site-directed mutagenesis, induced mutation, or may occur as allelic variants (polymorphisms).

As used herein, a "functional fragment" is a truncated regulatory sequence formed by one or more deletions from a larger regulatory element. For example, the 5' portion of a promoter up to the TATA box near the transcription start site can be deleted without abolishing promoter activity, as described by Opsahl-Sorteberg, et al., (2004) "Identification of a 49-bp fragment of the HvLTP2 promoter directing aleruone cell specific expression" *Gene* 341:49-58. Such fragments should retain promoter activity, particularly the ability to drive stress-induced expression. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis, et al., (1987) *Methods Enzymol.* 155:335-350, and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences in genomic DNA. Alternatively, the probe represents a fragment of the coding sequence natively associated with the promoter sequence. To achieve specific hybridization under a variety of conditions, such probes include sequences that are unique and are preferably at least about 10 nucleotides in length, and most preferably at least about 20 nucleotides in length. Such probes can be used to amplify corresponding sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see, e.g., Innis, et al., (1990) *PCR Protocols, A Guide to Methods and Applications*, eds., Academic Press).

The regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a promoter and a second sequence, wherein the promoter sequence initiates and mediates transcription of the DNA sequence corresponding to the second sequence. The expression cassette will include a regulatory sequence of the invention operably linked to at least one sequence of interest.

In one typical embodiment, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994, herein incorporated in its entirety by reference.

The regulatory elements of the invention can be operably linked in expression cassettes along with isolated nucleotide sequences of interest for expression in the plant. Such an expression cassette is provided with a plurality of restriction sites for insertion of the nucleotide sequence of interest under the transcriptional control of the regulatory elements.

The isolated nucleotides of interest expressed by the regulatory elements of the invention can be used for directing expression of a sequence in plant tissues. This can be achieved by increasing expression of endogenous or exogenous products. Alternatively, the results can be achieved by providing for a reduction of expression of one or more endogenous products, particularly enzymes or cofactors. This down regulation can be achieved through many different approaches known to one skilled in the art, including antisense, cosuppression, use of hairpin formations, or others, and discussed infra. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing synthesis of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of proteins, particularly modified proteins that improve the nutrient value of the plant, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,049 issued Dec. 30, 1997. Another example is lysine and/or sulfur-rich root protein encoded by the soybean 2S albumin described in WO 9735023 filed Mar. 20, 1996, and the chymotrypsin inhibitor from barley, Williamson, et al., (1987) *Eur. J. Biochem.* 165: 99-106.

Agronomic traits can be improved by altering expression of genes that: affect the response of root, plant or seed growth and development during environmental stress, Cheikh-N, et al., (1994) *Plant Physiol.* 106(1):45-51 and genes controlling carbohydrate metabolism to reduce kernel abortion in maize, Zinselmeier, et al., (1995) *Plant Physiol.* 107(2):385-391.

It is recognized that any gene of interest, including the native coding sequence, can be operably linked to the regulatory elements of the invention and expressed in the plant.

The following examples are offered by way of illustration and not by way of limitation.

EXPERIMENTAL

Example 1

Maize transformation

For example, immature maize embryos from greenhouse donor plants are bombarded with a plasmid containing a sequence, for example ZmSNAC1, operably linked to a constitutive promoter and further containing a selectable marker gene. Alternatively, the selectable marker gene is provided on a separate plasmid. Transformation is performed as follows. Media recipes follow below.

The ears are husked and surface-sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the ZmSNAC sequence operably linked to a constitutive promoter is made. This plasmid DNA plus plasmid DNA containing a selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the maintenance or increase of seed set during an abiotic stress episode.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite® gelling agent (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite® gelling agent (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® gelling agent (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l Bacto™-agar solidifying agent (added after bringing to volume with polished D-I $H_2O$), sterilized and cooled to 60° C.

Example 2

Soybean Embryo Transformation

Soybean embryos are bombarded with a plasmid containing the ZmSNAC1 polynucleotide operably linked to a constitutive promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188) and the 3' region of the nopaline synthase gene from the T-DNA of the Ti plasmid of Agrobacterium tumefaciens. The expression cassette comprising the ZmSNAC sequence as described above can be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M) and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 3

Rice Transformation

One method for transforming DNA into cells of higher plants that is available to those skilled in the art is high-velocity ballistic bombardment using metal particles coated with the nucleic acid constructs of interest (see, Klein, et al., Nature (1987) (London) 327:70-73 and see, U.S. Pat. No. 4,945,050). A Biolistic PDS-1000/He (BioRAD Laboratories, Hercules, Calif.) is used for these complementation experiments.

The bacterial hygromycin B phosphotransferase (Hpt II) gene from Streptomyces hygroscopicus that confers resistance to the antibiotic may be used as the selectable marker for rice transformation. In the vector, the Hpt II gene may be engineered with the 35S promoter from Cauliflower Mosaic Virus and the termination and polyadenylation signals from the octopine synthase gene of Agrobacterium tumefaciens. For example, see the description of vector pML18 in WO 97/47731, published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM $AgNO_3$) in the dark at 27-28° C. Embryogenic callus proliferating from the scutellum of the embryos is transferred to CM media (N6 salts, Nitsch and Nitsch vitamins, 1 mg/l 2,4-D, Chu, et al., (1985) Sci. Sinica 18:659-668). Callus cultures are maintained on CM by routine sub-culture at two-week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman® #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 (containing the selectable marker for rice transformation) onto the surface of gold particles. To accomplish this, a total of 10 µg of DNA at a 2:1 ratio of trait:selectable marker DNAs are added to 50 µl aliquot of gold particles that have been resuspended at a concentration of 60 mg $ml^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% Gelrite® gelling agent +50 ppm hyg B) for 2 weeks in the dark at 25° C. After 2 weeks the callus is transferred to RM2 media (MS salts, Nitsch and Nitsch vitamins, 3% sucrose, 0.4% Gelrite® gelling agent +50 ppm hyg B) and placed under cool white light (~40 $\mu Em^{-2}s^{-1}$) with a 12 hr photoperiod at 25° C. and 30-40% humidity. After 2-4 weeks in the light, callus begin to organize, and form shoots. Shoots are removed from surrounding callus/media and gently transferred to RM3 media (1/2×MS salts, Nitsch and Nitsch vitamins, 1% sucrose+50 ppm hygromycin B) in Phytatrays™ culture vessels (Sigma Chemical Co., St. Louis, Mo.) and incubation is continued using the same conditions as described in the previous step.

Plants are transferred from RM3 to 4" pots containing Scotts MetroMix® 350 growing medium after 2-3 weeks, when sufficient root and shoot growth have occurred.

Example 4

Variants of ZmSNAC

A. Variant ZmSNAC *Nucleotide Sequences That Do Not Alter the Encoded Amino Acid Sequence*

The ZmSNAC nucleotide sequences set forth in SEQ ID NO: 1, 3, 5, 7 and 9 are used to generate variant nucleotide sequences having the nucleotide sequence of the open reading frame with about 70%, 75%, 80%, 85%, 90% or 95% nucleotide sequence identity when compared to the corresponding starting unaltered ORF nucleotide sequence. These functional variants are generated using a standard codon table. While the nucleotide sequence of the variant is altered, the amino acid sequence encoded by the open reading frame does not change.

B. Variant Amino Acid Sequences of ZmSNAC1-5

Variant amino acid sequences of ZmSNAC1, ZmSNAC2, ZmSNAC3, ZmSNAC4 and ZmSNAC5 are generated. In this example, one or more amino acids are altered. Specifically, the open reading frame set forth in SEQ ID NO: 2, 4, 6, 8 or 10 is reviewed to determine the appropriate amino acid alteration. The selection of an amino acid to change is made by consulting a protein alignment with orthologs and other gene family members from various species. See, FIG. 1. An amino acid is selected that is deemed not to be under high selection pressure (not highly conserved) and which is rather easily substituted by an amino acid with similar chemical characteristics (i.e., similar functional side-chain). Assays as outlined elsewhere herein may be followed to confirm functionality. Variants having about 70%, 75%, 80%, 85%, 90% or 95% nucleic acid sequence identity to each of SEQ ID NO: 2, 4, 6, 8 and 10 are generated using this method.

C. Additional Variant Amino Acid Sequences of ZmSNAC Polypeptides

In this example, artificial protein sequences are created having 80%, 85%, 90% and 95% identity relative to the reference protein sequence. This latter effort requires identifying conserved and variable regions from the alignment set forth in FIG. 1 and then the judicious application of an amino acid substitutions table. These parts will be discussed in more detail below.

Largely, the determination of which amino acid sequences are altered is made based on the conserved regions among the ZmSNAC proteins or among the other ZmSNAC polypeptides. See, FIG. 1. Based on the sequence alignment, the various regions of the ZmSNAC polypeptides that can likely be altered can be determined. It is recognized that conservative substitutions can be made in the conserved regions without altering function. In addition, one of skill will understand that functional variants of the ZmSNAC sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 1.

First, any conserved amino acids in the protein that should not be changed are identified and "marked off" for insulation from the substitution. The start methionine will of course be added to this list automatically. Next, the changes are made.

H, C and P are not changed. The changes will occur with isoleucine first, sweeping N-terminal to C-terminal. Then leucine, and so on down the list until the desired target is reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of ZmSNAC1-5 are generated having about 82%, 87%, 92% and 97% amino acid identity to the starting unaltered ORF nucleotide sequence of SEQ ID NO: 2, 4, 6, 8 or 10.

TABLE 1

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |

TABLE 1-continued Substitution Table

| Amino Acid | Strongly Similar and Optimal Substitution | Rank of Order to Change | Comment |
| --- | --- | --- | --- |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

Example 5

Amplification of Additional ZmNAC Genes from Soybean or other Plant Species

Additional ZmNAC or ZmSNAC genes from plant species could be identified by PCR or RT-PCR methods using degenerate primers such as the ones described below. Degenerate primers can be designed against conserved amino acid motifs found in available ZmNAC proteins from soybean, maize, rice or *Arabidopsis*. Such motifs can be identified from an alignment of the protein sequences. Sense/antisense primers could be used in different combinations. Similarly, several rounds of PCR could be used. The product of amplification of one pair of sense/antisense primers could be used as template for PCR with another set of internal (nested) degenerate primers therefore maximizing the chances for amplification of an appropriate sequence, i.e., containing a sequence corresponding to the corresponding amino acid motif.

Example 6

Transformation of *Zea mays* by *Agrobacterium*

For *Agrobacterium*-mediated transformation of maize, the method of Zhao is employed (U.S. Pat. No. 5,981,840 and PCT patent publication WO98/32326; the contents of which are hereby incorporated by reference). Briefly, immature embryos are isolated from maize and the embryos contacted with a suspension of *Agrobacterium*, where the bacteria are capable of transferring the expression cassette to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 7

Activity of the ZmSNAC1 Promoter

To demonstrate that the DNA sequence isolated as the ZmSNAC1 promoter functions as a promoter, transgenic maize assays were performed. These assays provided a rapid assessment of whether the DNA sequence tested is able to direct gene expression.

The full length promoter (see, SEQ ID NO: 11) was PCR amplified from genomic DNA and cloned in an expression cassette as a translational fusion with B-glucuronidase (GUS; see, Jefferson, et al., (1987) *EMBO J* 16:3901 and U.S. Pat. No. 5,599,670). Transgenic plants were created by *Agrobacterium*-mediated transformation (see, Example 7) of the expression cassette into rapid-cycling maize as described in US Patent Application Publication 2003/0221212.

Leaf or stalk tissue was excised from T0 plants for analysis of ZmSNAC1 promoter activity. GUS expression was determined by immersing the excised plant tissues in either (1) a GUS staining buffer modified from Jefferson, et al., (1987 *Plant Mol. Biol. Rep.* 5:387-405) containing 1.36 g $NaH_2PO_4$, 1.74 g $Na_2HPO_4$, 164 mg $K_4Fe(CN)_6 3H_2O$, 211 mg $K_3Fe(CN)_6$, 0.06 ml Triton X-100 and 50 mg X-Gluc (Sodium Salt) in a final volume of 100 ml, or (2) a GUS staining buffer of McCabe, et al., (McCabe and Martinell, (1993) *Bio/Technol.* 11:596-598) containing 1.36 g $NaH_2PO_4$, 1.74 g $Na_2HPO_4$, 16.4 mg $K_4Fe(CN)_6 3H_2O$, 0.29 g EDTA, 0.2 ml Triton X-100 and 50 mg X-Gluc (Sodium Salt) in a final volume of 100 ml. The plant tissue was incubated in the dark overnight at 37° C. Replacing the GUS staining solution with 70% ethanol stopped the assay. GUS activity was quantified using plant extract and expressed as nmoles/mg total protein/hour; see, Côté and Rutledge (2003) *Plant Cell Rep* 21(6):619-624. Ten non-transgenic control events were also tested. Seven of the ten transgene-positive events (Events 1.1, 1.2, 1.3, 1.4, 2.5, 1.7, 1.10) showed significant GUS staining in a range of activity levels; see, FIG. 2. The ten control events did not show any significant GUS staining.

To further confirm that the ZmSNAC1 promoter can be induced by stress, excised tissue was incubated in 5 μM abscisic acid (ABA) for 16 hours and GUS expression was again evaluated as described above. ABA treatment resulted in increased staining in the seven previously-identified events, as shown in FIG. 2.

These data confirm the promoter function and stress-inducible nature of SEQ ID NO: 11 and its endogenous gene ZmSNAC1.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a first polynucleotide which initiates transcription of a second, operably-linked, heterologous polynucleotide in a plant cell, wherein the first polynucleotide comprises the nucleotide sequence of SEQ ID NO: 11, and wherein said nucleotide sequence exhibits stress inducible promoter activity.

2. An expression cassette comprising the first and second polynucleotides of claim 1.

3. A plant cell having stably incorporated into its genome the expression cassette of claim 2.

4. A plant having stably incorporated into its genome the expression cassette of claim 2.

* * * * *

SEQUENCE LISTING

```
<160> NUMBER OF SEQ ID NOS: 22

<210> SEQ ID NO 1
<211> LENGTH: 1232
<212> TYPE: DNA
<213> ORGANISM: Zea mays
<220> FEATURE:
<221> NAME/KEY: CDS
<222> LOCATION: (199)...(1134)

<400> SEQUENCE: 1
atcgacgagc gccagccgcc agcagccgag ccggagcgac cttttctttt ttcttttaca      60
cagcgggacg gagaaaggag tcaatcagcc aaagccaccc accgctttta cccaccgatc     120
ggcgttgccg ccgctagcat tgtcggcttc agctccatcc aaatccaccg ccagcaagca     180
agcaagcaag ccggcgcc atg ggt ctg ccg atg agg agg gag agg gac gcg       231
                    Met Gly Leu Pro Met Arg Arg Glu Arg Asp Ala
                      1               5                  10 gag gcg gag ctg aac ctg ccg ccg ggg ttc cgg ttc cac ccc acc gac       279
Glu Ala Glu Leu Asn Leu Pro Pro Gly Phe Arg Phe His Pro Thr Asp
             15                  20                  25 gac gag ctg gtg gag cac tac ctg tgc cgc aag gcg gcg ggg cag cgc       327
Asp Glu Leu Val Glu His Tyr Leu Cys Arg Lys Ala Ala Gly Gln Arg
         30                  35                  40 ctc ccc gtg ccc atc atc gcc gag gtg gac ctg tac agg ttc gac ccc       375
Leu Pro Val Pro Ile Ile Ala Glu Val Asp Leu Tyr Arg Phe Asp Pro
     45                  50                  55 tgg gac ctg ccg gag cgc gcg ctc ttc ggg gcc cgc gag tgg tac ttc       423
Trp Asp Leu Pro Glu Arg Ala Leu Phe Gly Ala Arg Glu Trp Tyr Phe
 60                  65                  70                  75 ttc acg ccc agg gac cgc aag tac ccc aac ggc tcc cgc ccc aac cgc       471
Phe Thr Pro Arg Asp Arg Lys Tyr Pro Asn Gly Ser Arg Pro Asn Arg
                 80                  85                  90 gcc gcc ggc aac ggg tac tgg aag gcc acc ggc gcc gac aag ccc gtc       519
Ala Ala Gly Asn Gly Tyr Trp Lys Ala Thr Gly Ala Asp Lys Pro Val
             95                 100                 105 gcg ccg cgc ggc cgc acg ctc ggg atc aag aag gcg ctc gtc ttc tac       567
Ala Pro Arg Gly Arg Thr Leu Gly Ile Lys Lys Ala Leu Val Phe Tyr
        110                 115                 120 gcc ggc aag gcg ccg cgc ggg gtc aag acg gac tgg atc atg cac gag       615
Ala Gly Lys Ala Pro Arg Gly Val Lys Thr Asp Trp Ile Met His Glu
    125                 130                 135 tac agg ctc gcc gac gcc ggc cgc gcc gcc gcc gcc aag aag ggg tcg       663
Tyr Arg Leu Ala Asp Ala Gly Arg Ala Ala Ala Ala Lys Lys Gly Ser
140                 145                 150                 155 ctt agg ttg gat gac tgg gtg ctg tgc cgg ctg tac aac aag aag aac       711
Leu Arg Leu Asp Asp Trp Val Leu Cys Arg Leu Tyr Asn Lys Lys Asn
                160                 165                 170 gag tgg gag aag atg cag ctg ggg aag acc gcc gtc gcc ggc gtc ggc       759
Glu Trp Glu Lys Met Gln Leu Gly Lys Thr Ala Val Ala Gly Val Gly
            175                 180                 185
```

```
gcc acc aag gag gag gcg atg gac atg gcc acc tcg cac acg cac tcc    807
Ala Thr Lys Glu Glu Ala Met Asp Met Ala Thr Ser His Thr His Ser
        190                 195                 200 cac tcc caa tca cac tcg cac tcg tgg ggc gag acg cgc acg cca gag    855
His Ser Gln Ser His Ser His Ser Trp Gly Glu Thr Arg Thr Pro Glu
    205                 210                 215 tcg gag atc gtg gac aac gac ccg ttc ccg gag ctg gac tcg ttc ccg    903
Ser Glu Ile Val Asp Asn Asp Pro Phe Pro Glu Leu Asp Ser Phe Pro
220                 225                 230                 235 gcg ttc cag gac ccg gcg atg atg atg acg gtg ccc aag gag gag cag    951
Ala Phe Gln Asp Pro Ala Met Met Met Thr Val Pro Lys Glu Glu Gln
            240                 245                 250 gtg gac ggc tgc agc gcc aag agc ggc aac ctg ttc gtg gac ctc agc    999
Val Asp Gly Cys Ser Ala Lys Ser Gly Asn Leu Phe Val Asp Leu Ser
        255                 260                 265 tac gac gac atc cag ggc atg tac agc ggc ctc gac atg ctg ccg ccg   1047
Tyr Asp Asp Ile Gln Gly Met Tyr Ser Gly Leu Asp Met Leu Pro Pro
    270                 275                 280 ccc ggg gag gac ttc tac tcc tcg ctc ttc gcg tct ccc agg gtc aag   1095
Pro Gly Glu Asp Phe Tyr Ser Ser Leu Phe Ala Ser Pro Arg Val Lys
285                 290                 295 ggg aac cag ccc gcc gga gcc gcc ggg ttg gga cag ttc tgagctgagg    1144
Gly Asn Gln Pro Ala Gly Ala Ala Gly Leu Gly Gln Phe
300                 305                 310 cgaggatgga gccatggatc aggagatgaa gacggttgcg aactctgtaa atacagcata  1204
ggagtcgaac ctgaccctga cccttgtt                                    1232

<210> SEQ ID NO 2
<211> LENGTH: 312
<212> TYPE: PRT
<213> ORGANISM: Zea mays

<400> SEQUENCE: 2

Met Gly Leu Pro Met Arg Arg Glu Arg Asp Ala Glu Ala Glu Leu Asn
1               5                   10                  15

Leu Pro Pro Gly Phe Arg Phe His Pro Thr Asp Asp Glu Leu Val Glu
            20                  25                  30

His Tyr Leu Cys Arg Lys Ala Ala Gly Gln Arg Leu Pro Val Pro Ile
        35                  40                  45

Ile Ala Glu Val Asp Leu Tyr Arg Phe Asp Pro Trp Asp Leu Pro Glu
    50                  55                  60

Arg Ala Leu Phe Gly Ala Arg Glu Trp Tyr Phe Phe Thr Pro Arg Asp
65                  70                  75                  80

Arg Lys Tyr Pro Asn Gly Ser Arg Pro Asn Arg Ala Ala Gly Asn Gly
                85                  90                  95

Tyr Trp Lys Ala Thr Gly Ala Asp Lys Pro Val Ala Pro Arg Gly Arg
            100                 105                 110

Thr Leu Gly Ile Lys Lys Ala Leu Val Phe Tyr Ala Gly Lys Ala Pro
        115                 120                 125

Arg Gly Val Lys Thr Asp Trp Ile Met His Glu Tyr Arg Leu Ala Asp
    130                 135                 140

Ala Gly Arg Ala Ala Ala Lys Lys Gly Ser Leu Arg Leu Asp Asp
145                 150                 155                 160

Trp Val Leu Cys Arg Leu Tyr Asn Lys Asn Glu Trp Glu Lys Met
                165                 170                 175

Gln Leu Gly Lys Thr Ala Val Ala Gly Val Gly Ala Thr Lys Glu Glu
            180                 185                 190
```

```
Ala Met Asp Met Ala Thr Ser His Thr His Ser His Ser Gln Ser His
            195                 200                 205

Ser His Ser Trp Gly Glu Thr Arg Thr Pro Glu Ser Glu Ile Val Asp
    210                 215                 220

Asn Asp Pro Phe Pro Glu Leu Asp Ser Phe Pro Ala Phe Gln Asp Pro
225                 230                 235                 240

Ala Met Met Met Thr Val Pro Lys Glu Glu Val Asp Gly Cys Ser
                245                 250                 255

Ala Lys Ser Gly Asn Leu Phe Val Asp Leu Ser Tyr Asp Asp Ile Gln
            260                 265                 270

Gly Met Tyr Ser Gly Leu Asp Met Leu Pro Pro Gly Glu Asp Phe
        275                 280                 285

Tyr Ser Ser Leu Phe Ala Ser Pro Arg Val Lys Gly Asn Gln Pro Ala
    290                 295                 300

Gly Ala Ala Gly Leu Gly Gln Phe
305                 310

<210> SEQ ID NO 3
<211> LENGTH: 1325
<212> TYPE: DNA
<213> ORGANISM: Zea mays
<220> FEATURE:
<221> NAME/KEY: CDS
<222> LOCATION: (182)...(1057)

<400> SEQUENCE: 3
```

| | |
|---|---|
| cccgcccaca ggacaggaca cacagagccg agccacccca cccaccatcg gcgaccagca | 60 |
| gccagccgcg ggagcgagct gtttaaagac accgagtcgg agtcggacgg aggactggca | 120 |
| ggcacaaccg aagccaccgc ttctagttct cgggttcatc gccagcaatc cagaccacat | 180 |

```
a atg gga ctg ccg gtg acg agg agg agg gag agg gac gcg gag gcg gag        229
  Met Gly Leu Pro Val Thr Arg Arg Arg Glu Arg Asp Ala Glu Ala Glu
    1               5                   10                  15 ctg gac ctg ccg ccg ggg ttc cgg ttc cac ccc acc gac gac gag ctg        277
Leu Asp Leu Pro Pro Gly Phe Arg Phe His Pro Thr Asp Asp Glu Leu
            20                  25                  30 gtg gag cac tac ctg tgc cgc aag gcg gcg ggg cag cgc ctc ccc gtg        325
Val Glu His Tyr Leu Cys Arg Lys Ala Ala Gly Gln Arg Leu Pro Val
        35                  40                  45 ccc atc atc gcc gag gtg gac ctg tac agg ttc gac ccc tgg gac ctg        373
Pro Ile Ile Ala Glu Val Asp Leu Tyr Arg Phe Asp Pro Trp Asp Leu
    50                  55                  60 ccg gag cgc gcg ctc ttc ggg gcc cgg gag tgg tac ttc ttc acg ccc        421
Pro Glu Arg Ala Leu Phe Gly Ala Arg Glu Trp Tyr Phe Phe Thr Pro
65                  70                  75                  80 agg gac cgc aag tac ccc aac ggc tcc cgc ccc aac cgc gcc gcc ggc        469
Arg Asp Arg Lys Tyr Pro Asn Gly Ser Arg Pro Asn Arg Ala Ala Gly
                85                  90                  95 gac gga tac tgg aag gcc acc ggc gcc gac aag ccc gtc gcg ccg cgc        517
Asp Gly Tyr Trp Lys Ala Thr Gly Ala Asp Lys Pro Val Ala Pro Arg
            100                 105                 110 ggc gcc cgc acg ctc ggg atc aag aag gcg ctc gtc ttc tac gcc ggc        565
Gly Ala Arg Thr Leu Gly Ile Lys Lys Ala Leu Val Phe Tyr Ala Gly
        115                 120                 125 aag gcg ccg cgc ggg gtc aag acg gac tgg atc atg cac gag tac agg        613
Lys Ala Pro Arg Gly Val Lys Thr Asp Trp Ile Met His Glu Tyr Arg
    130                 135                 140 ctc gct gac gcc ggc cgc cgc gcc aag aaa ggg tcg ctc agg ttg gat        661
```

```
Leu Ala Asp Ala Gly Arg Arg Ala Lys Lys Gly Ser Leu Arg Leu Asp
145                 150                 155                 160 gac tgg gtg ctg tgc cgg ctg tac aac aag aag aac gag tgg gag aag      709
Asp Trp Val Leu Cys Arg Leu Tyr Asn Lys Lys Asn Glu Trp Glu Lys
                165                 170                 175 atg cgg ctg ggg aag gag ggc gcc gcc aaa gag gag gcc atg gac atg      757
Met Arg Leu Gly Lys Glu Gly Ala Ala Lys Glu Glu Ala Met Asp Met
            180                 185                 190 agc acc tcc cac tcg tgg ggc gag acg cgc acg ccg gag tcg gag atc      805
Ser Thr Ser His Ser Trp Gly Glu Thr Arg Thr Pro Glu Ser Glu Ile
        195                 200                 205 gtg gac aac gac ccg ccg ttc ccg gat ccg ccg gcg ccg gcg atg atg      853
Val Asp Asn Asp Pro Pro Phe Pro Asp Pro Pro Ala Pro Ala Met Met
210                 215                 220 gtg ccc aag aag gag cgg gtg gac gcc ggc ggc agc gcc agg agc agc      901
Val Pro Lys Lys Glu Arg Val Asp Ala Gly Gly Ser Ala Arg Ser Ser
225                 230                 235                 240 gac ctg ttc gtg gat ctc agc tac gac gac atc cag ggc atg tac agc      949
Asp Leu Phe Val Asp Leu Ser Tyr Asp Asp Ile Gln Gly Met Tyr Ser
                245                 250                 255 ggc ctc gac atg ctg ccg ccg ccc ggc gag gac ttc tac tcc tcg ctc      997
Gly Leu Asp Met Leu Pro Pro Pro Gly Glu Asp Phe Tyr Ser Ser Leu
            260                 265                 270 ttc gcg tcg ccc agg gtc agg ggg aac cag ccc acc gga gcc gcg ggg     1045
Phe Ala Ser Pro Arg Val Arg Gly Asn Gln Pro Thr Gly Ala Ala Gly
        275                 280                 285 ttg ggc ccc ttc tgagtgagct caggcgagga tggaggcatg agatgagga           1097
Leu Gly Pro Phe
            290 gagaagacgg acggcgttgc gaactctgta aatacagcat aggactagga gtcgaacctg    1157 gtcggggtta caagtcgagt gtgtcggtgt tcgtacatg ggagccggcc cggtctttgg     1217 cttggcgctg gctcattctt tagtttcact tcctgcgcag acggtaggta gatgtgtatg    1277 cgtagctgtg cactatcact tcctcttcaa cagaaccgat tcactccg                1325

<210> SEQ ID NO 4
<211> LENGTH: 292
<212> TYPE: PRT
<213> ORGANISM: Zea mays

<400> SEQUENCE: 4

Met Gly Leu Pro Val Thr Arg Arg Glu Arg Asp Ala Glu Ala Glu
1               5                   10                  15

Leu Asp Leu Pro Pro Gly Phe Arg Phe His Pro Thr Asp Asp Glu Leu
            20                  25                  30

Val Glu His Tyr Leu Cys Arg Lys Ala Ala Gly Gln Arg Leu Pro Val
        35                  40                  45

Pro Ile Ile Ala Glu Val Asp Leu Tyr Arg Phe Asp Pro Trp Asp Leu
    50                  55                  60

Pro Glu Arg Ala Leu Phe Gly Ala Arg Glu Trp Tyr Phe Phe Thr Pro
65                  70                  75                  80

Arg Asp Arg Lys Tyr Pro Asn Gly Ser Arg Pro Asn Arg Ala Ala Gly
                85                  90                  95

Asp Gly Tyr Trp Lys Ala Thr Gly Ala Asp Lys Pro Val Ala Pro Arg
            100                 105                 110

Gly Ala Arg Thr Leu Gly Ile Lys Lys Ala Leu Val Phe Tyr Ala Gly
        115                 120                 125
```

```
Lys Ala Pro Arg Gly Val Lys Thr Asp Trp Ile Met His Glu Tyr Arg
        130                 135                 140

Leu Ala Asp Ala Gly Arg Arg Ala Lys Lys Gly Ser Leu Arg Leu Asp
145                 150                 155                 160

Asp Trp Val Leu Cys Arg Leu Tyr Asn Lys Lys Asn Glu Trp Glu Lys
                165                 170                 175

Met Arg Leu Gly Lys Glu Gly Ala Ala Lys Glu Glu Ala Met Asp Met
            180                 185                 190

Ser Thr Ser His Ser Trp Gly Glu Thr Arg Thr Pro Glu Ser Glu Ile
        195                 200                 205

Val Asp Asn Asp Pro Pro Phe Pro Asp Pro Ala Pro Ala Met Met
210                 215                 220

Val Pro Lys Lys Glu Arg Val Asp Ala Gly Ser Ala Arg Ser
225                 230                 235                 240

Asp Leu Phe Val Asp Leu Ser Tyr Asp Ile Gln Gly Met Tyr Ser
                245                 250                 255

Gly Leu Asp Met Leu Pro Pro Gly Glu Asp Phe Tyr Ser Ser Leu
            260                 265                 270

Phe Ala Ser Pro Arg Val Arg Gly Asn Gln Pro Thr Gly Ala Ala Gly
                275                 280                 285

Leu Gly Pro Phe
    290

<210> SEQ ID NO 5
<211> LENGTH: 1376
<212> TYPE: DNA
<213> ORGANISM: Zea mays
<220> FEATURE:
<221> NAME/KEY: CDS
<222> LOCATION: (180)...(1085)

<400> SEQUENCE: 5
cggacgcgtg ggcggacgcg tgggggccgag ccaccccacc caccatcggc gaccagcagc      60
cagccgcggg agcgagctgt ttaaagacac cgagtcggag tcggacggag gactggcagg     120
cacaaccgaa gccaccgctt ctagttctcg ggttcatcgc cagcaatcca gaccacata      179 atg gga cag ccg gtg acg agg agg agg gag agg gac gcg gag gcg gag       227
Met Gly Gln Pro Val Thr Arg Arg Arg Glu Arg Asp Ala Glu Ala Glu
1               5                   10                  15 ctg gac ctg ccg ccg ggg ttc cgg ttc cac ccc aca gac gac gag ctg       275
Leu Asp Leu Pro Pro Gly Phe Arg Phe His Pro Thr Asp Asp Glu Leu
            20                  25                  30 gtg gag cac tac ctg tgc cgc aag gcg gcg ggg cag cgc ctc ccc gtg       323
Val Glu His Tyr Leu Cys Arg Lys Ala Ala Gly Gln Arg Leu Pro Val
        35                  40                  45 ccc atc atc gcc gag gtg gac ctg tac agg ttc gac ccg tgg gac ctg       371
Pro Ile Ile Ala Glu Val Asp Leu Tyr Arg Phe Asp Pro Trp Asp Leu
    50                  55                  60 ccg gag cgc gcg ctc ttc ggg gcc cgg gag tgg tac ttc ttc acg ccc       419
Pro Glu Arg Ala Leu Phe Gly Ala Arg Glu Trp Tyr Phe Phe Thr Pro
65                  70                  75                  80 agg gac cgc aag tac ccc aac ggc tcc cgc ccc aac cgc gcc gcc ggc       467
Arg Asp Arg Lys Tyr Pro Asn Gly Ser Arg Pro Asn Arg Ala Ala Gly
                85                  90                  95 gac ggg tac tgg aag gcc acc ggc gcc gac aag ccc gtc gcg ccg cgc       515
Asp Gly Tyr Trp Lys Ala Thr Gly Ala Asp Lys Pro Val Ala Pro Arg
            100                 105                 110 gcc gcc gcc gcc gac gcc cgc acg ctc ggg atc aag aag gcg ctc gtc       563
```

```
             Ala Ala Ala Asp Ala Arg Thr Leu Gly Ile Lys Lys Ala Leu Val
                     115                 120                 125 ttc tac gcc ggc aag gcg ccg cgc ggg gtc aag aca gac tgg atc atg           611
Phe Tyr Ala Gly Lys Ala Pro Arg Gly Val Lys Thr Asp Trp Ile Met
        130                 135                 140 cac gag tac agg ctc gct gac gcc ggc cgc gcc aag aag ggg tcg               659
His Glu Tyr Arg Leu Ala Asp Ala Gly Arg Ala Lys Lys Gly Ser
145                 150                 155                 160 ctc agg ttg gat gac tgg gtg ctg tgc cgg ctg tac aac aag aag aac           707
Leu Arg Leu Asp Asp Trp Val Leu Cys Arg Leu Tyr Asn Lys Lys Asn
                    165                 170                 175 gag tgg gag aag atg cgg ctg ggg aag ggg gca gcc gcc ggc gca gtc           755
Glu Trp Glu Lys Met Arg Leu Gly Lys Gly Ala Ala Ala Gly Ala Val
                180                 185                 190 aaa gag gag gag gcc atg gac atg agc acc tcc cac tcg cag atc acc           803
Lys Glu Glu Glu Ala Met Asp Met Ser Thr Ser His Ser Gln Ile Thr
            195                 200                 205 cac tcg tgg ggc gag acg cgc acg ccg gag tcg gag atc gtg gac aac           851
His Ser Trp Gly Glu Thr Arg Thr Pro Glu Ser Glu Ile Val Asp Asn
        210                 215                 220 gac ctg ccg ttc ccg gat ccg gcg atg atg gtg ccc aag aag gag cgg           899
Asp Leu Pro Phe Pro Asp Pro Ala Met Met Val Pro Lys Lys Glu Arg
225                 230                 235                 240 gtg gac gac ggc ggc agc gcc agg acc agc gac ctg ttc gtg gat ctc           947
Val Asp Asp Gly Gly Ser Ala Arg Thr Ser Asp Leu Phe Val Asp Leu
                    245                 250                 255 agc tac gac gac atc caa ggc atg tac agc ggc ctc gac atg ctg ccg           995
Ser Tyr Asp Asp Ile Gln Gly Met Tyr Ser Gly Leu Asp Met Leu Pro
                260                 265                 270 ccg gcc ggc gag gac ttg tac tcc tcg ctc ttc gcg tcg ccc agg gtc           1043
Pro Ala Gly Glu Asp Leu Tyr Ser Ser Leu Phe Ala Ser Pro Arg Val
            275                 280                 285 agg ggg aac cag ccc acc gga ccc gcg ggg ttg ggc ccc ttc                   1085
Arg Gly Asn Gln Pro Thr Gly Pro Ala Gly Leu Gly Pro Phe
        290                 295                 300 tgagtgagct caggcgagga tggaggcatg gagatcagga gagaagacgg acggcgttgc         1145
caactctgta aatacagcat aggacgagga gtcgaacctg actgaacctg gtcggggtta        1205
caagtcgagt gtgtcggtgt ttcgtacatg ggaaccgggc cttacatggg agccggcccg        1265
gtcttggttt ggcgctggct cattctttag tttcacttcc tgcgcagacg gtagatgtgt        1325
atgcatagct gttcactatc acttcctctt caacagaacc gattcactcc g                1376

<210> SEQ ID NO 6
<211> LENGTH: 302
<212> TYPE: PRT
<213> ORGANISM: Zea mays

<400> SEQUENCE: 6

Met Gly Gln Pro Val Thr Arg Arg Arg Glu Arg Asp Ala Glu Ala Glu
1               5                   10                  15

Leu Asp Leu Pro Pro Gly Phe Arg Phe His Pro Thr Asp Glu Leu
            20                  25                  30

Val Glu His Tyr Leu Cys Arg Lys Ala Ala Gly Gln Arg Leu Pro Val
        35                  40                  45

Pro Ile Ile Ala Glu Val Asp Leu Tyr Arg Phe Asp Pro Trp Asp Leu
    50                  55                  60

Pro Glu Arg Ala Leu Phe Gly Ala Arg Glu Trp Tyr Phe Phe Thr Pro
65                  70                  75                  80
```

-continued

```
Arg Asp Arg Lys Tyr Pro Asn Gly Ser Arg Pro Asn Arg Ala Ala Gly
                85                  90                  95

Asp Gly Tyr Trp Lys Ala Thr Gly Ala Asp Lys Pro Val Ala Pro Arg
            100                 105                 110

Ala Ala Ala Ala Asp Ala Arg Thr Leu Gly Ile Lys Lys Ala Leu Val
        115                 120                 125

Phe Tyr Ala Gly Lys Ala Pro Arg Gly Val Lys Thr Asp Trp Ile Met
    130                 135                 140

His Glu Tyr Arg Leu Ala Asp Ala Gly Arg Arg Ala Lys Lys Gly Ser
145                 150                 155                 160

Leu Arg Leu Asp Asp Trp Val Leu Cys Arg Leu Tyr Asn Lys Lys Asn
                165                 170                 175

Glu Trp Glu Lys Met Arg Leu Gly Lys Gly Ala Ala Gly Ala Val
            180                 185                 190

Lys Glu Glu Ala Met Asp Met Ser Thr Ser His Ser Gln Ile Thr
        195                 200                 205

His Ser Trp Gly Glu Thr Arg Thr Pro Glu Ser Glu Ile Val Asp Asn
    210                 215                 220

Asp Leu Pro Phe Pro Asp Pro Ala Met Met Val Pro Lys Lys Glu Arg
225                 230                 235                 240

Val Asp Asp Gly Gly Ser Ala Arg Thr Ser Asp Leu Phe Val Asp Leu
                245                 250                 255

Ser Tyr Asp Asp Ile Gln Gly Met Tyr Ser Gly Leu Asp Met Leu Pro
            260                 265                 270

Pro Ala Gly Glu Asp Leu Tyr Ser Ser Leu Phe Ala Ser Pro Arg Val
        275                 280                 285

Arg Gly Asn Gln Pro Thr Gly Pro Ala Gly Leu Gly Pro Phe
    290                 295                 300

<210> SEQ ID NO 7
<211> LENGTH: 1522
<212> TYPE: DNA
<213> ORGANISM: Zea mays
<220> FEATURE:
<221> NAME/KEY: CDS
<222> LOCATION: (64)...(948)
<223> OTHER INFORMATION: ZmSNAC4

<400> SEQUENCE: 7
taccattagc agtagccaca gccagaacac cagcagacag cagcatcagc agggaggaac      60 acg atg agc ggc gcc ggt ccg gat ctg cag ctg cca ccg ggg ttc cgg      108
    Met Ser Gly Ala Gly Pro Asp Leu Gln Leu Pro Pro Gly Phe Arg
    1               5                   10                  15 ttc cac ccg acg gac gag gag ctg gtg atg cac tac ctc tgc cgc cgc      156
Phe His Pro Thr Asp Glu Glu Leu Val Met His Tyr Leu Cys Arg Arg
                20                  25                  30 tgc gcc ggc ctg ccc atc gcc gtc ccc atc atc gcc gag atc gac ctc      204
Cys Ala Gly Leu Pro Ile Ala Val Pro Ile Ile Ala Glu Ile Asp Leu
            35                  40                  45 tac aag ttc gac cca tgg cag ctc cca agg atg gcg ctg tac ggc gag      252
Tyr Lys Phe Asp Pro Trp Gln Leu Pro Arg Met Ala Leu Tyr Gly Glu
        50                  55                  60 aag gag tgg tac ttc ttc tcc ccg cgg gac cgc aag tac ccg aac ggg      300
Lys Glu Trp Tyr Phe Phe Ser Pro Arg Asp Arg Lys Tyr Pro Asn Gly
    65                  70                  75 tcc agg ccc aac cgc gcc gcc ggg gct ggg tac tgg aag gcc acc ggc      348
Ser Arg Pro Asn Arg Ala Ala Gly Ala Gly Tyr Trp Lys Ala Thr Gly
```

```
                80                   85                   90                   95
gct gac aag ccc gtg ggc acg ccc aag ccg ctg gcc atc aag aag gcg      396
Ala Asp Lys Pro Val Gly Thr Pro Lys Pro Leu Ala Ile Lys Lys Ala
            100                 105                 110 ctc gtc ttc tac gcc ggc aag gcg ccc aag ggc gag aag acc aac tgg      444
Leu Val Phe Tyr Ala Gly Lys Ala Pro Lys Gly Glu Lys Thr Asn Trp
        115                 120                 125 atc atg cac gag tac cgc ctc gcc gac gtc gac cgc tcg gcg cgc aag      492
Ile Met His Glu Tyr Arg Leu Ala Asp Val Asp Arg Ser Ala Arg Lys
    130                 135                 140 aag aac agc ctc agg ttg gat gac tgg gtc ctg tgc cgc atc tac aac      540
Lys Asn Ser Leu Arg Leu Asp Asp Trp Val Leu Cys Arg Ile Tyr Asn
145                 150                 155 aag aag ggc ggc ggg ctg gag aag gcg gcg gcg ccg gcg gcc ggc ggc      588
Lys Lys Gly Gly Gly Leu Glu Lys Ala Ala Ala Pro Ala Ala Gly Gly
160                 165                 170                 175 gac cac aag cct gtg ttc gcc acg gcg gcg gtg agc tcc ccg ccg gag      636
Asp His Lys Pro Val Phe Ala Thr Ala Ala Val Ser Ser Pro Pro Glu
            180                 185                 190 cag aag ccg ttc gtg gcg gcg gcg ggc ggg ctg ccc ccg gcg ttc ccg      684
Gln Lys Pro Phe Val Ala Ala Ala Gly Gly Leu Pro Pro Ala Phe Pro
        195                 200                 205 gag ctg gcg gcg tac tac gac cgg ccg tcg gac tcg atg ccg cgg ctg      732
Glu Leu Ala Ala Tyr Tyr Asp Arg Pro Ser Asp Ser Met Pro Arg Leu
    210                 215                 220 cac gcg gac tac tcc agc tgc tcg gag cag gtg ctg tcc ccg gag cag      780
His Ala Asp Tyr Ser Ser Cys Ser Glu Gln Val Leu Ser Pro Glu Gln
225                 230                 235 ctg gcg tgc gac cgg gag gtg cag agc cag ccc aag atc agc gag tgg      828
Leu Ala Cys Asp Arg Glu Val Gln Ser Gln Pro Lys Ile Ser Glu Trp
240                 245                 250                 255 gag cgg acc ttc gcc tcc gac ccc gtg aac ccc gcg ggc tcc atg ctc      876
Glu Arg Thr Phe Ala Ser Asp Pro Val Asn Pro Ala Gly Ser Met Leu
            260                 265                 270 gac ccc gtc gtc ggc cac gcc ggc ggc gac ccg ctg ctg cag gac atc      924
Asp Pro Val Val Gly His Ala Gly Gly Asp Pro Leu Leu Gln Asp Ile
        275                 280                 285 ctc atg tac tgg ggc aag ccg ttc tagacgacac cgcccatcat gtcctgaggg     978
Leu Met Tyr Trp Gly Lys Pro Phe
    290                 295 gaggtggggg tggcgaagca tcctcggctg cggttggttg gttgattgat ctgtcttggg   1038
cagcgcaatg caatgcaacc gcacggtgtg ggctttgact caggcgagcc gccattgttg   1098
acttgcaagg aggatataat atgaaactat agctggatta catggagagg cggcaatgag   1158
accgtctggc cccgccggaa gggagacgga gacggagacg gatggcgcag tgcatcgggt   1218
gtggtggatc gtgcgcggca tgtgtgtgtg tggctgtaca tatacatact gtacatgatt   1278
ggttcagtgc agggtttctg ttccttcatt gattagttat tatactaata agtactagta   1338
attttgtaag ggcttgtagt tgcagtctcc gtactggtgg taggtagtgc aggccatatt   1398
cgtcatcgcc aagcttcgag tgtacttact cctacaatat atttttaca gtatatattg    1458 tagctgtgtt ggctcttccg gaaaaaaaat ggaagggaa aataggggatt atgttatttt   1518 gatt                                                                1522

<210> SEQ ID NO 8
<211> LENGTH: 295
<212> TYPE: PRT
<213> ORGANISM: Zea mays
```

<400> SEQUENCE: 8

Met Ser Gly Ala Gly Pro Asp Leu Gln Leu Pro Pro Gly Phe Arg Phe
1               5                   10                  15

His Pro Thr Asp Glu Glu Leu Val Met His Tyr Leu Cys Arg Arg Cys
            20                  25                  30

Ala Gly Leu Pro Ile Ala Val Pro Ile Ile Ala Glu Ile Asp Leu Tyr
        35                  40                  45

Lys Phe Asp Pro Trp Gln Leu Pro Arg Met Ala Leu Tyr Gly Glu Lys
    50                  55                  60

Glu Trp Tyr Phe Phe Ser Pro Arg Asp Arg Lys Tyr Pro Asn Gly Ser
65                  70                  75                  80

Arg Pro Asn Arg Ala Ala Gly Ala Gly Tyr Trp Lys Ala Thr Gly Ala
                85                  90                  95

Asp Lys Pro Val Gly Thr Pro Lys Pro Leu Ala Ile Lys Lys Ala Leu
            100                 105                 110

Val Phe Tyr Ala Gly Lys Ala Pro Lys Gly Glu Lys Thr Asn Trp Ile
        115                 120                 125

Met His Glu Tyr Arg Leu Ala Asp Val Asp Arg Ser Ala Arg Lys Lys
    130                 135                 140

Asn Ser Leu Arg Leu Asp Asp Trp Val Leu Cys Arg Ile Tyr Asn Lys
145                 150                 155                 160

Lys Gly Gly Gly Leu Glu Lys Ala Ala Ala Pro Ala Ala Gly Gly Asp
                165                 170                 175

His Lys Pro Val Phe Ala Thr Ala Ala Val Ser Ser Pro Pro Glu Gln
            180                 185                 190

Lys Pro Phe Val Ala Ala Gly Gly Leu Pro Pro Ala Phe Pro Glu
        195                 200                 205

Leu Ala Ala Tyr Tyr Asp Arg Pro Ser Asp Ser Met Pro Arg Leu His
    210                 215                 220

Ala Asp Tyr Ser Ser Cys Ser Glu Gln Val Leu Ser Pro Glu Gln Leu
225                 230                 235                 240

Ala Cys Asp Arg Glu Val Gln Ser Gln Pro Lys Ile Ser Glu Trp Glu
                245                 250                 255

Arg Thr Phe Ala Ser Asp Pro Val Asn Pro Ala Gly Ser Met Leu Asp
            260                 265                 270

Pro Val Val Gly His Ala Gly Gly Asp Pro Leu Leu Gln Asp Ile Leu
        275                 280                 285

Met Tyr Trp Gly Lys Pro Phe
    290                 295

<210> SEQ ID NO 9
<211> LENGTH: 1405
<212> TYPE: DNA
<213> ORGANISM: Zea mays
<220> FEATURE:
<221> NAME/KEY: CDS
<222> LOCATION: (128)...(1144)
<223> OTHER INFORMATION: ZmSNAC5

<400> SEQUENCE: 9
aaagtggtcg aatcggcggc tgatttgacc cggctcgcta ttagagctgc gaaagtgatc        60
cgagcagtca cggtttcgga agcggcgcgt cggccggagg agaaacgcaa ccagctgtcg       120 aggagct atg agc agc ggt ggc gga ggc aga gtg ccg gcg gcg gcg gcg         169
        Met Ser Ser Gly Gly Gly Gly Arg Val Pro Ala Ala Ala Ala
        1               5                   10

-continued

| | |
|---|---|
| gcg cag tcg cag gag ctg cag cta ccg ccg ggg ttc cgg ttc cac ccg<br>Ala Gln Ser Gln Glu Leu Gln Leu Pro Pro Gly Phe Arg Phe His Pro<br>15                              20                         25                       30 | 217 |
| acg gat gag gag ctg gtg gtg cac tac ctc tgc cgg cgc tgc gcc ggg<br>Thr Asp Glu Glu Leu Val Val His Tyr Leu Cys Arg Arg Cys Ala Gly<br>               35                       40                       45 | 265 |
| ctg ccc atc tcc gtg ccc atc atc gcc gag gtc gac cta tac aag cac<br>Leu Pro Ile Ser Val Pro Ile Ile Ala Glu Val Asp Leu Tyr Lys His<br>              50                      55                      60 | 313 |
| gat ccc tgg cag ctc cca agg atg gcg ctg tac ggc gag aag gag tgg<br>Asp Pro Trp Gln Leu Pro Arg Met Ala Leu Tyr Gly Glu Lys Glu Trp<br>65                              70                         75 | 361 |
| tac ttc ttc tcc ccg cgg gac cgc aag tac ccg aac ggg tcg cgg ccg<br>Tyr Phe Phe Ser Pro Arg Asp Arg Lys Tyr Pro Asn Gly Ser Arg Pro<br>         80                       85                      90 | 409 |
| aac cgc gcc gcc ggc gcc ggg tac tgg aag gcc acc ggc gca gac aag<br>Asn Arg Ala Ala Gly Ala Gly Tyr Trp Lys Ala Thr Gly Ala Asp Lys<br>95                            100                      105                110 | 457 |
| ccg gtg ggc acg ccg aag ccg gtg gcc atc aag aag gct ctc gtc ttc<br>Pro Val Gly Thr Pro Lys Pro Val Ala Ile Lys Lys Ala Leu Val Phe<br>                 115                      120                      125 | 505 |
| tac gcc ggc aag gcg ccc aag ggc gac aag acc aac tgg atc atg cat<br>Tyr Ala Gly Lys Ala Pro Lys Gly Asp Lys Thr Asn Trp Ile Met His<br>              130                      135                      140 | 553 |
| gag tac cgc ctc gcc gac gtc gac cgc acc gcc cgc aag aag aac aac<br>Glu Tyr Arg Leu Ala Asp Val Asp Arg Thr Ala Arg Lys Lys Asn Asn<br>                145                      150                      155 | 601 |
| agc ctc agg ttg gat gat tgg gtg ctg tgc cga atc tac aac aag aaa<br>Ser Leu Arg Leu Asp Asp Trp Val Leu Cys Arg Ile Tyr Asn Lys Lys<br>160                              165                      170 | 649 |
| ggc gcg ctg gag aag ccg acc gga gcc ggc ggc agg gcc gag gcc agc<br>Gly Ala Leu Glu Lys Pro Thr Gly Ala Gly Gly Arg Ala Glu Ala Ser<br>175                            180                      185                190 | 697 |
| agc cag ggc gcg ctg ggg tcc atg tcc atg ggc tcg ccg ccg gag cag<br>Ser Gln Gly Ala Leu Gly Ser Met Ser Met Gly Ser Pro Pro Glu Gln<br>                195                      200                      205 | 745 |
| aag ccg tcc gtg ctg ccg tct gcc acg gca acg gca acg gcc gcg gcc<br>Lys Pro Ser Val Leu Pro Ser Ala Thr Ala Thr Ala Thr Ala Ala Ala<br>210                              215                      220 | 793 |
| ggg acg ggg tac gcg ccg ctg ccg ttc tcg gag ctg gcg gcg tac tac<br>Gly Thr Gly Tyr Ala Pro Leu Pro Phe Ser Glu Leu Ala Ala Tyr Tyr<br>                225                      230                      235 | 841 |
| gag gtc cgg ccg tcc gac tcg atg ccc cgg gcg cac ggc gcg gac tcg<br>Glu Val Arg Pro Ser Asp Ser Met Pro Arg Ala His Gly Ala Asp Ser<br>240                              245                      250 | 889 |
| agc tgc tcg ggc cac gcg ctg gcc gcc acg tcg tcg tgc ggc ggc ggc<br>Ser Cys Ser Gly His Ala Leu Ala Ala Thr Ser Ser Cys Gly Gly Gly<br>255                              260                      265                270 | 937 |
| ggc ggc gag cgg cct gag gta cag agc cag ccc aag atc gcc gag tgg<br>Gly Gly Glu Arg Pro Glu Val Gln Ser Gln Pro Lys Ile Ala Glu Trp<br>                275                      280                      285 | 985 |
| gag cgc act ttc gcc gcc ggc gcc ggc ccg gga atc aac ccg gcc ggc<br>Glu Arg Thr Phe Ala Ala Gly Ala Gly Pro Gly Ile Asn Pro Ala Gly<br>                290                      295                      300 | 1033 |
| tcg atg ctg ggg ctt ggg ggg cat cag ctc ggc tcc gcg gcg gtg ggg<br>Ser Met Leu Gly Leu Gly Gly His Gln Leu Gly Ser Ala Ala Val Gly<br>305                              310                      315 | 1081 |
| gta ggg ctg ccc gcc ggc gac ccg ctg ctc cag gac atc ctc aca tac<br>Val Gly Leu Pro Ala Gly Asp Pro Leu Leu Gln Asp Ile Leu Thr Tyr | 1129 |

```
                320             325             330
tgg ggc aag ccg tac tgagaaagat gactggtccg agccgccggc gatgaggcca       1184
Trp Gly Lys Pro Tyr
335 tgtcggcttg tgaatgatca tggagctgga ctacaggatt attgctgcta cgagttgaat     1244 taaactgttt atatgcgatt gatttggtac tgggattttt gtatacttga attagtactc    1304 tctctatata gagagacata cacatactcg agtatatatg ttttgcttat atatagagta    1364 tggaataata tttatatctg ctggtccatc ctgcaacccg c                        1405
```

<210> SEQ ID NO 10
<211> LENGTH: 339
<212> TYPE: PRT
<213> ORGANISM: Zea mays

<400> SEQUENCE: 10

```
Met Ser Ser Gly Gly Gly Gly Arg Val Pro Ala Ala Ala Ala Gln
  1               5                  10                  15

Ser Gln Glu Leu Gln Leu Pro Pro Gly Phe Arg Phe His Pro Thr Asp
             20                  25                  30

Glu Glu Leu Val Val His Tyr Leu Cys Arg Arg Cys Ala Gly Leu Pro
         35                  40                  45

Ile Ser Val Pro Ile Ile Ala Glu Val Asp Leu Tyr Lys His Asp Pro
     50                  55                  60

Trp Gln Leu Pro Arg Met Ala Leu Tyr Gly Glu Lys Glu Trp Tyr Phe
 65                  70                  75                  80

Phe Ser Pro Arg Asp Arg Lys Tyr Pro Asn Gly Ser Arg Pro Asn Arg
                 85                  90                  95

Ala Ala Gly Ala Gly Tyr Trp Lys Ala Thr Gly Ala Asp Lys Pro Val
            100                 105                 110

Gly Thr Pro Lys Pro Val Ala Ile Lys Lys Ala Leu Val Phe Tyr Ala
        115                 120                 125

Gly Lys Ala Pro Lys Gly Asp Lys Thr Asn Trp Ile Met His Glu Tyr
    130                 135                 140

Arg Leu Ala Asp Val Asp Arg Thr Ala Arg Lys Lys Asn Asn Ser Leu
145                 150                 155                 160

Arg Leu Asp Asp Trp Val Leu Cys Arg Ile Tyr Asn Lys Lys Gly Ala
                165                 170                 175

Leu Glu Lys Pro Thr Gly Ala Gly Gly Arg Ala Glu Ala Ser Ser Gln
            180                 185                 190

Gly Ala Leu Gly Ser Met Ser Met Gly Ser Pro Glu Gln Lys Pro
        195                 200                 205

Ser Val Leu Pro Ser Ala Thr Ala Thr Ala Ala Ala Gly Thr
    210                 215                 220

Gly Tyr Ala Pro Leu Pro Phe Ser Glu Leu Ala Ala Tyr Tyr Glu Val
225                 230                 235                 240

Arg Pro Ser Asp Ser Met Pro Arg Ala His Gly Ala Asp Ser Cys
                245                 250                 255

Ser Gly His Ala Leu Ala Ala Thr Ser Ser Cys Gly Gly Gly Gly
            260                 265                 270

Glu Arg Pro Glu Val Gln Ser Gln Pro Lys Ile Ala Glu Trp Glu Arg
        275                 280                 285

Thr Phe Ala Ala Gly Ala Gly Pro Gly Ile Asn Pro Ala Gly Ser Met
    290                 295                 300
```

```
Leu Gly Leu Gly Gly His Gln Leu Gly Ser Ala Ala Val Gly Val Gly
305                 310                 315                 320

Leu Pro Ala Gly Asp Pro Leu Leu Gln Asp Ile Leu Thr Tyr Trp Gly
                325                 330                 335

Lys Pro Tyr

<210> SEQ ID NO 11
<211> LENGTH: 1625
<212> TYPE: DNA
<213> ORGANISM: Zea mays
<220> FEATURE:
<221> NAME/KEY: promoter
<222> LOCATION: (1)...(1625)
<223> OTHER INFORMATION: ZmSNAC1 promoter

<400> SEQUENCE: 11
gcccttattt ctgtctgtct ctctctcccc cctctcccgt gcggggcact ggcagcgccg      60
ccgccggggt cacaggggcg ggactcgtgt cgacgcgcgg caggcccgcg caccacgtgc     120
ccatatatac aaaaaaaaaa gattggccct atcattggcg cgccgcctgc ctgtcttggg     180
catgtgtctc gcgcggcgtg gtggcttgat ctccacgtac gccgggcgtg gcactgtcgg     240 gggggggtggg gggggggggg gggggggggt ggatcgtgtc gctacgccta cggccgcccg     300
agcgaattgc gtggcggaac gagggagata gggatgctga ggcagcggcg ggcgaatcat     360
ctggatgcat gcatgcgcag cgtgcacgta ggtgctcgcg attccgacga aacgcatgca     420
tgatagatag ggtgtaaacg tccctagctg caactagtg gtgggggtta tggttatctg     480
ctattgccaa ttcttgtgct cctcgatcgt ctacgcgtgc tgcgacggct gcacacgtac     540
tcctaggtta tggtggagat tttgtcccat gtccataccc atggaaacat ttttttgttac    600 atagccgtac cctaataggc gaatttcaca tgagttgatg ggtatcgggt tccaattgac     660
atctctacct gccatcatcg tttcgtaacc gtgaaaaaga aacacacgta cgccacgctt     720
tgcgtatact tgtagcacga taatgaaccc tctgggtgaa aggaccactc gtcggtcggt     780
ccacagaccg cttgctgtac gtggctcgtg aagaatttat tttgatgaac aaaatgaaat     840
ccaacccacg ggaggcatgt gttgtgtact ccatgcatgc acccgcgccg aaaaagaaag     900
agattccctt ctagcccatg ccgtctcggc cggtggtggg ccctcccccc agagcccaac     960
cccaatccgc atgaaacgga gcagcatccc cggccatatc ccgagcgcgc ctgcacggcc    1020
acagaagaac cacgccgccc gagagcaacc gccgctgcaa aagcgaatcc gtcccaattc    1080
agctgaggtc ggccgtgacg ccaaccccgc ggtcccgtcc aatccaatcc tgggccgctg    1140
aggtggccat ccacgggcct ccctccctcc ccccacctt ccccgaaggc ccgaacccac     1200
caggccacca cctcatccag ctgccccgc ccaaccacac gtgccaattc cgctttcgcg     1260
cagccgccga ctcgctttga cccccatccc gcatccccta tccccgagga agcttccaga    1320
ccgcccgcgc ccgccgctat atatccctct cctgcgcgcg gttctcagct tcgacaacac    1380
cgcgcgcgca atacacggga cacacacgca gatccgagct aaccaccatc gacgagcgcc    1440
agccgccagc agccgagccg gagcgacctt ttcttttttc ttttacacag cgggacggag    1500
aaaggagtca atcagccaaa gccacccacc gcttttaccc accgatcggc gttgccgccg    1560
ctagcattgt cggcttcagc tccatccaaa tccaccgcca gcaagcaagc aagcaagccg    1620
gcgcc                                                                1625

<210> SEQ ID NO 12
<211> LENGTH: 317
```

```
<212> TYPE: PRT
<213> ORGANISM: Arabidopsis

<400> SEQUENCE: 12

Met Gly Ile Gln Glu Thr Asp Pro Leu Thr Gln Leu Ser Leu Pro Pro
1               5                   10                  15

Gly Phe Arg Phe Tyr Pro Thr Asp Glu Glu Leu Met Val Gln Tyr Leu
            20                  25                  30

Cys Arg Lys Ala Ala Gly Tyr Asp Phe Ser Leu Gln Leu Ile Ala Glu
                35                  40                  45

Ile Asp Leu Tyr Lys Phe Asp Pro Trp Val Leu Pro Asn Lys Ala Leu
50                  55                  60

Phe Gly Glu Lys Glu Trp Tyr Phe Phe Ser Pro Arg Asp Arg Lys Tyr
65                  70                  75                  80

Pro Asn Gly Ser Arg Pro Asn Arg Val Ala Gly Ser Gly Tyr Trp Lys
                85                  90                  95

Ala Thr Gly Thr Asp Lys Ile Ile Ser Thr Glu Gly Gln Arg Val Gly
            100                 105                 110

Ile Lys Lys Ala Leu Val Phe Tyr Ile Gly Lys Ala Pro Lys Gly Thr
            115                 120                 125

Lys Thr Asn Trp Ile Met His Glu Tyr Arg Leu Ile Glu Pro Ser Arg
130                 135                 140

Arg Asn Gly Ser Thr Lys Leu Asp Asp Trp Val Leu Cys Arg Ile Tyr
145                 150                 155                 160

Lys Lys Gln Ser Ser Ala Gln Lys Gln Val Tyr Asp Asn Gly Ile Ala
                165                 170                 175

Asn Ala Arg Glu Phe Ser Asn Asn Gly Thr Ser Ser Thr Thr Ser Ser
            180                 185                 190

Ser Ser His Phe Glu Asp Val Leu Asp Ser Phe His Gln Glu Ile Asp
        195                 200                 205

Asn Arg Asn Phe Gln Phe Ser Asn Pro Asn Arg Ile Ser Ser Leu Arg
210                 215                 220

Pro Asp Leu Thr Glu Gln Lys Thr Gly Phe His Gly Leu Ala Asp Thr
225                 230                 235                 240

Ser Asn Phe Asp Trp Ala Ser Phe Ala Gly Asn Val Glu His Asn Asn
                245                 250                 255

Ser Val Pro Glu Leu Gly Met Ser His Val Val Pro Asn Leu Glu Tyr
            260                 265                 270

Asn Cys Gly Tyr Leu Lys Thr Glu Glu Val Glu Ser Ser His Gly
            275                 280                 285

Phe Asn Asn Ser Gly Glu Leu Ala Gln Lys Tyr Gly Val Asp Ser
290                 295                 300

Phe Gly Tyr Ser Gly Gln Val Gly Gly Phe Gly Phe Met
305                 310                 315

<210> SEQ ID NO 13
<211> LENGTH: 283
<212> TYPE: PRT
<213> ORGANISM: Arabidopsis

<400> SEQUENCE: 13

Met Lys Ser Glu Leu Asn Leu Pro Ala Gly Phe Arg Phe His Pro Thr
1               5                   10                  15

Asp Glu Glu Leu Val Lys Phe Tyr Leu Cys Arg Lys Cys Ala Ser Glu
            20                  25                  30
```

```
Gln Ile Ser Ala Pro Val Ile Ala Glu Ile Asp Leu Tyr Lys Phe Asn
        35                  40                  45

Pro Trp Glu Leu Pro Glu Met Ser Leu Tyr Gly Lys Glu Trp Tyr
 50                  55                  60

Phe Phe Ser Pro Arg Asp Arg Lys Tyr Pro Asn Gly Ser Arg Pro Asn
 65                  70                  75                  80

Arg Ala Ala Gly Thr Gly Tyr Trp Lys Ala Thr Gly Ala Asp Lys Pro
                 85                  90                  95

Ile Gly Lys Pro Lys Thr Leu Gly Ile Lys Lys Ala Leu Val Phe Tyr
            100                 105                 110

Ala Gly Lys Ala Pro Lys Gly Ile Lys Thr Asn Trp Ile Met His Glu
        115                 120                 125

Tyr Arg Leu Ala Asn Val Asp Arg Ser Ala Ser Val Asn Lys Lys Asn
    130                 135                 140

Asn Leu Arg Leu Asp Asp Trp Val Leu Cys Arg Ile Tyr Asn Lys Lys
145                 150                 155                 160

Gly Thr Met Glu Lys Tyr Phe Pro Ala Asp Glu Lys Pro Arg Thr Thr
                165                 170                 175

Thr Met Ala Glu Gln Ser Ser Ser Pro Phe Asp Thr Ser Asp Ser Thr
            180                 185                 190

Tyr Pro Thr Leu Gln Glu Asp Ser Ser Ser Gly Gly His Gly
        195                 200                 205

His Val Val Ser Pro Asp Val Leu Glu Val Gln Ser Glu Pro Lys Trp
    210                 215                 220

Gly Glu Leu Glu Asp Ala Leu Glu Ala Phe Asp Thr Ser Met Phe Gly
225                 230                 235                 240

Ser Ser Met Glu Leu Leu Gln Pro Asp Ala Phe Val Pro Gln Phe Leu
                245                 250                 255

Tyr Gln Ser Asp Tyr Phe Thr Ser Phe Gln Asp Pro Pro Glu Gln Lys
            260                 265                 270

Pro Phe Leu Asn Trp Ser Phe Ala Pro Gln Gly
        275                 280

<210> SEQ ID NO 14
<211> LENGTH: 289
<212> TYPE: PRT
<213> ORGANISM: Arabidopsis

<400> SEQUENCE: 14

Met Ser Glu Leu Leu Gln Leu Pro Pro Gly Phe Arg Phe His Pro Thr
 1               5                  10                  15

Asp Glu Glu Leu Val Met His Tyr Leu Cys Arg Lys Cys Ala Ser Gln
            20                  25                  30

Ser Ile Ala Val Pro Ile Ile Ala Glu Ile Asp Leu Tyr Lys Tyr Asp
        35                  40                  45

Pro Trp Glu Leu Pro Gly Leu Ala Leu Tyr Gly Glu Lys Glu Trp Tyr
 50                  55                  60

Phe Phe Ser Pro Arg Asp Arg Lys Tyr Pro Asn Gly Ser Arg Pro Asn
 65                  70                  75                  80

Arg Ser Ala Gly Ser Gly Tyr Trp Lys Ala Thr Gly Ala Asp Lys Pro
                 85                  90                  95

Ile Gly Leu Pro Lys Pro Val Gly Ile Lys Lys Ala Leu Val Phe Tyr
            100                 105                 110

Ala Gly Lys Ala Pro Lys Gly Glu Lys Thr Asn Trp Ile Met His Glu
        115                 120                 125
```

```
Tyr Arg Leu Ala Asp Val Asp Arg Ser Val Arg Lys Lys Lys Asn Ser
    130                 135                 140

Leu Arg Leu Asp Asp Trp Val Leu Cys Arg Ile Tyr Asn Lys Lys Gly
145                 150                 155                 160

Ala Thr Glu Arg Arg Gly Pro Pro Pro Val Val Tyr Gly Asp Glu
                165                 170                 175

Ile Met Glu Glu Lys Pro Lys Val Thr Glu Met Val Met Pro Pro
            180                 185                 190

Pro Gln Gln Thr Ser Glu Phe Ala Tyr Phe Asp Thr Ser Asp Ser Val
            195                 200                 205

Pro Lys Leu His Thr Thr Asp Ser Ser Cys Ser Glu Gln Val Val Ser
    210                 215                 220

Pro Glu Phe Thr Ser Glu Val Gln Ser Glu Pro Lys Trp Lys Asp Trp
225                 230                 235                 240

Ser Ala Val Ser Asn Asp Asn Asn Thr Leu Asp Phe Gly Phe Asn
                245                 250                 255

Tyr Ile Asp Ala Thr Val Asp Asn Ala Phe Gly Gly Gly Ser Ser
            260                 265                 270

Asn Gln Met Phe Pro Leu Gln Asp Met Phe Met Tyr Met Gln Lys Pro
        275                 280                 285

Tyr

<210> SEQ ID NO 15
<211> LENGTH: 268
<212> TYPE: PRT
<213> ORGANISM: Arabidopsis

<400> SEQUENCE: 15

Met Glu Val Thr Ser Gln Ser Thr Leu Pro Pro Gly Phe Arg Phe His
1               5                   10                  15

Pro Thr Asp Glu Glu Leu Ile Val Tyr Tyr Leu Arg Asn Gln Thr Met
                20                  25                  30

Ser Lys Pro Cys Pro Val Ser Ile Ile Pro Glu Val Asp Ile Tyr Lys
            35                  40                  45

Phe Asp Pro Trp Gln Leu Pro Glu Lys Thr Glu Phe Gly Glu Asn Glu
        50                  55                  60

Trp Tyr Phe Phe Ser Pro Arg Glu Arg Lys Tyr Pro Asn Gly Val Arg
65                  70                  75                  80

Pro Asn Arg Ala Ala Val Ser Gly Tyr Trp Lys Ala Thr Gly Thr Asp
                85                  90                  95

Lys Ala Ile His Ser Gly Ser Ser Asn Val Gly Val Lys Lys Ala Leu
            100                 105                 110

Val Phe Tyr Lys Gly Arg Pro Pro Lys Gly Ile Lys Thr Asp Trp Ile
        115                 120                 125

Met His Glu Tyr Arg Leu His Asp Ser Arg Lys Ala Ser Thr Lys Arg
    130                 135                 140

Asn Gly Ser Met Arg Leu Asp Glu Trp Val Leu Cys Arg Ile Tyr Lys
145                 150                 155                 160

Lys Arg Gly Ala Ser Lys Leu Leu Asn Glu Gln Glu Gly Phe Met Asp
                165                 170                 175

Glu Val Leu Met Glu Asp Glu Thr Lys Val Val Asn Glu Ala Glu
            180                 185                 190

Arg Arg Thr Glu Glu Glu Ile Met Met Met Thr Ser Met Lys Leu Pro
        195                 200                 205
```

```
Arg Thr Cys Ser Leu Ala His Leu Leu Glu Met Asp Tyr Met Gly Pro
    210                 215                 220

Val Ser His Ile Asp Asn Phe Ser Gln Phe Asp His Leu His Gln Pro
225                 230                 235                 240

Asp Ser Glu Ser Ser Trp Phe Gly Asp Leu Gln Phe Asn Gln Asp Glu
                245                 250                 255

Ile Leu Asn His His Arg Gln Ala Met Phe Lys Phe
            260                 265

<210> SEQ ID NO 16
<211> LENGTH: 320
<212> TYPE: PRT
<213> ORGANISM: Arabidopsis

<400> SEQUENCE: 16

Met Glu Ser Thr Asp Ser Ser Gly Gly Pro Pro Pro Gln Pro Asn
1               5                   10                  15

Leu Pro Pro Gly Phe Arg Phe His Pro Thr Asp Glu Glu Leu Val Ile
                20                  25                  30

His Tyr Leu Lys Arg Lys Ala Asp Ser Val Pro Leu Pro Val Ala Ile
            35                  40                  45

Ile Ala Asp Val Asp Leu Tyr Lys Phe Asp Pro Trp Glu Leu Pro Ala
50                  55                  60

Lys Ala Ser Phe Gly Glu Gln Glu Trp Tyr Phe Phe Ser Pro Arg Asp
65                  70                  75                  80

Arg Lys Tyr Pro Asn Gly Ala Arg Pro Asn Arg Ala Ala Thr Ser Gly
                85                  90                  95

Tyr Trp Lys Ala Thr Gly Thr Asp Lys Pro Val Ile Ser Thr Gly Gly
            100                 105                 110

Gly Gly Ser Lys Lys Val Gly Val Lys Ala Leu Val Phe Tyr Ser
        115                 120                 125

Gly Lys Pro Pro Lys Gly Val Lys Ser Asp Trp Ile Met His Glu Tyr
    130                 135                 140

Arg Leu Thr Asp Asn Lys Pro Thr His Ile Cys Asp Phe Gly Asn Lys
145                 150                 155                 160

Lys Asn Ser Leu Arg Leu Asp Asp Trp Val Leu Cys Arg Ile Tyr Lys
                165                 170                 175

Lys Asn Asn Ser Thr Ala Ser Arg His His His Leu His His Ile
            180                 185                 190

His Leu Asp Asn Asp His His Arg His Asp Met Met Ile Asp Asp Asp
        195                 200                 205

Arg Phe Arg His Val Pro Pro Gly Leu His Phe Pro Ala Ile Phe Ser
    210                 215                 220

Asp Asn Asn Asp Pro Thr Ala Ile Tyr Asp Gly Gly Gly Gly Tyr
225                 230                 235                 240

Gly Gly Gly Ser Tyr Ser Met Asn His Cys Phe Ala Ser Gly Ser Lys
                245                 250                 255

Gln Glu Gln Leu Phe Pro Pro Val Met Met Thr Ser Leu Asn Gln
            260                 265                 270

Asp Ser Gly Ile Gly Ser Ser Ser Pro Ser Lys Arg Phe Asn Gly
        275                 280                 285

Gly Gly Val Gly Asp Cys Ser Thr Ser Met Ala Ala Thr Pro Leu Met
    290                 295                 300

Gln Asn Gln Gly Gly Ile Tyr Gln Leu Pro Gly Leu Asn Trp Tyr Ser
```

<210> SEQ ID NO 17
<211> LENGTH: 451
<212> TYPE: PRT
<213> ORGANISM: Arabidopsis

<400> SEQUENCE: 17

```
Met Lys Glu Asp Met Glu Val Leu Ser Leu Ala Ser Leu Pro Val Gly
 1               5                  10                  15

Phe Arg Phe Ser Pro Thr Asp Glu Glu Leu Val Arg Tyr Tyr Leu Arg
                20                  25                  30

Leu Lys Ile Asn Gly His Asp Asn Asp Val Arg Val Ile Arg Glu Ile
            35                  40                  45

Asp Ile Cys Lys Trp Glu Pro Trp Asp Leu Pro Asp Phe Ser Val Val
        50                  55                  60

Lys Thr Thr Asp Ser Glu Trp Leu Phe Phe Cys Pro Leu Asp Arg Lys
 65                 70                  75                  80

Tyr Pro Ser Gly Ser Arg Met Asn Arg Ala Thr Val Ala Gly Tyr Trp
                85                  90                  95

Lys Ala Thr Gly Lys Asp Arg Lys Ile Lys Ser Gly Lys Thr Lys Ile
                100                 105                 110

Ile Gly Val Lys Arg Thr Leu Val Phe Tyr Thr Gly Arg Ala Pro Lys
            115                 120                 125

Gly Thr Arg Thr Cys Trp Ile Met His Glu Tyr Arg Ala Thr Glu Lys
        130                 135                 140

Asp Leu Asp Gly Thr Lys Ser Gly Gln Asn Pro Phe Val Val Cys Lys
145                 150                 155                 160

Leu Phe Lys Lys Gln Asp Ile Val Asn Gly Ala Ala Glu Pro Glu Glu
                165                 170                 175

Ser Lys Ser Cys Glu Val Glu Pro Ala Val Ser Ser Pro Thr Val Val
                180                 185                 190

Asp Glu Val Glu Met Ser Glu Val Ser Pro Val Phe Pro Lys Thr Glu
            195                 200                 205

Glu Thr Asn Pro Cys Asp Val Ala Glu Ser Ser Leu Val Ile Pro Ser
        210                 215                 220

Glu Cys Arg Ser Gly Tyr Ser Val Pro Glu Val Thr Thr Thr Gly Leu
225                 230                 235                 240

Asp Asp Ile Asp Trp Leu Ser Phe Met Glu Phe Asp Ser Pro Lys Leu
                245                 250                 255

Phe Ser Pro Leu His Ser Gln Val Gln Ser Glu Leu Gly Ser Ser Phe
                260                 265                 270

Asn Gly Leu Gln Ser Glu Ser Ser Glu Leu Phe Lys Asn His Asn Glu
            275                 280                 285

Asp Tyr Ile Gln Thr Gln Tyr Gly Thr Asn Asp Ala Asp Glu Tyr Met
        290                 295                 300

Ser Lys Phe Leu Asp Ser Phe Leu Asp Ile Pro Tyr Glu Pro Glu Gln
305                 310                 315                 320

Ile Pro Tyr Glu Pro Gln Asn Leu Ser Ser Cys Asn Lys Ile Asn Asp
                325                 330                 335

Glu Ser Lys Arg Gly Ile Lys Ile Arg Ala Arg Ala Gln Ala Pro
                340                 345                 350

Gly Cys Ala Glu Gln Phe Val Met Gln Gly Asp Ala Ser Arg Arg Leu
        355                 360                 365
```

```
Arg Leu Gln Val Asn Leu Asn Ser His Lys Ser Glu Thr Asp Ser Thr
    370                 375                 380

Gln Leu Gln Phe Ile Lys Lys Glu Val Lys Asp Thr Thr Thr Glu Thr
385                 390                 395                 400

Met Thr Lys Gly Cys Gly Asn Phe Thr Arg Ser Lys Ser Arg Thr Ser
                405                 410                 415

Phe Ile Phe Lys Lys Ile Ala Ala Met Gly Cys Ser Tyr Arg Gly Leu
                420                 425                 430

Phe Arg Val Gly Val Val Ala Val Cys Val Met Ser Val Cys Ser
                435                 440                 445

Leu Val Ala
    450

<210> SEQ ID NO 18
<211> LENGTH: 375
<212> TYPE: PRT
<213> ORGANISM: Arabidopsis

<400> SEQUENCE: 18

Met Asp Ile Pro Tyr Tyr His Tyr Asp His Gly Gly Asp Ser Gln Tyr
1               5                   10                  15

Leu Pro Pro Gly Phe Arg Phe His Pro Thr Asp Glu Glu Leu Ile Thr
                20                  25                  30

His Tyr Leu Leu Arg Lys Val Leu Asp Gly Cys Phe Ser Ser Arg Ala
            35                  40                  45

Ile Ala Glu Val Asp Leu Asn Lys Cys Glu Pro Trp Gln Leu Pro Gly
    50                  55                  60

Arg Ala Lys Met Gly Glu Lys Glu Trp Tyr Phe Phe Ser Leu Arg Asp
65                  70                  75                  80

Arg Lys Tyr Pro Thr Gly Leu Arg Thr Asn Arg Ala Thr Glu Ala Gly
                85                  90                  95

Tyr Trp Lys Ala Thr Gly Lys Asp Arg Glu Ile Phe Ser Ser Lys Thr
            100                 105                 110

Cys Ala Leu Val Gly Met Lys Lys Thr Leu Val Phe Tyr Lys Gly Arg
        115                 120                 125

Ala Pro Lys Gly Glu Lys Ser Asn Trp Val Met His Glu Tyr Arg Leu
    130                 135                 140

Glu Gly Lys Phe Ser Tyr His Phe Ile Ser Arg Ser Ser Lys Asp Glu
145                 150                 155                 160

Trp Val Ile Ser Arg Val Phe Gln Lys Thr Thr Leu Ala Ser Thr Gly
                165                 170                 175

Ala Val Ser Glu Gly Gly Gly Gly Gly Ala Thr Val Ser Val Ser
            180                 185                 190

Ser Gly Thr Gly Pro Ser Lys Lys Thr Lys Val Pro Ser Thr Ile Ser
        195                 200                 205

Arg Asn Tyr Gln Glu Gln Pro Ser Ser Pro Ser Ser Val Ser Leu Pro
    210                 215                 220

Pro Leu Leu Asp Pro Thr Thr Leu Gly Tyr Thr Asp Ser Ser Cys
225                 230                 235                 240

Ser Tyr Asp Ser Arg Ser Thr Asn Thr Val Thr Ala Ser Ala Ile
                245                 250                 255

Thr Glu His Val Ser Cys Phe Ser Thr Val Pro Thr Thr Thr Ala
            260                 265                 270

Leu Gly Leu Asp Val Asn Ser Phe Ser Arg Leu Pro Pro Pro Leu Gly
        275                 280                 285
```

```
Phe Asp Phe Asp Pro Phe Pro Arg Phe Val Ser Arg Asn Val Ser Thr
    290                 295                 300

Gln Ser Asn Phe Arg Ser Phe Gln Glu Asn Phe Asn Gln Phe Pro Tyr
305                 310                 315                 320

Phe Gly Ser Ser Ser Ala Ser Thr Met Thr Ser Ala Val Asn Leu Pro
                325                 330                 335

Ser Phe Gln Gly Gly Gly Val Ser Gly Met Asn Tyr Trp Leu Pro
            340                 345                 350

Ala Thr Ala Glu Glu Asn Glu Ser Lys Val Gly Val Leu His Ala Gly
            355                 360                 365

Leu Asp Cys Ile Trp Asn Tyr
    370                 375

<210> SEQ ID NO 19
<211> LENGTH: 310
<212> TYPE: PRT
<213> ORGANISM: Arabidopsis

<400> SEQUENCE: 19

Met Asp Val Asp Val Phe Asn Gly Trp Gly Arg Pro Arg Phe Glu Asp
1               5                   10                  15

Glu Ser Leu Met Pro Pro Gly Phe Arg Phe His Pro Thr Asp Glu Glu
                20                  25                  30

Leu Ile Thr Tyr Tyr Leu Leu Lys Lys Val Leu Asp Ser Asn Phe Ser
            35                  40                  45

Cys Ala Ala Ile Ser Gln Val Asp Leu Asn Lys Ser Glu Pro Trp Glu
        50                  55                  60

Leu Pro Glu Lys Ala Lys Met Gly Glu Lys Glu Trp Tyr Phe Phe Thr
65                  70                  75                  80

Leu Arg Asp Arg Lys Tyr Pro Thr Gly Leu Arg Thr Asn Arg Ala Thr
                85                  90                  95

Glu Ala Gly Tyr Trp Lys Ala Thr Gly Lys Asp Arg Glu Ile Lys Ser
            100                 105                 110

Ser Lys Thr Lys Ser Leu Leu Gly Met Lys Lys Thr Leu Val Phe Tyr
        115                 120                 125

Lys Gly Arg Ala Pro Lys Gly Glu Lys Ser Cys Trp Val Met His Glu
130                 135                 140

Tyr Arg Leu Asp Gly Lys Phe Ser Tyr His Tyr Ile Ser Ser Ser Ala
145                 150                 155                 160

Lys Asp Glu Trp Val Leu Cys Lys Val Cys Leu Lys Ser Gly Val Val
                165                 170                 175

Ser Arg Glu Thr Asn Leu Ile Ser Ser Ser Ser Ser Ala Val Thr
            180                 185                 190

Gly Glu Phe Ser Ser Ala Gly Ser Ala Ile Ala Pro Ile Ile Asn Thr
        195                 200                 205

Phe Ala Thr Glu His Val Ser Cys Phe Ser Asn Asn Ser Ala Ala His
    210                 215                 220

Thr Asp Ala Ser Phe His Thr Phe Leu Pro Ala Pro Pro Ser Leu
225                 230                 235                 240

Pro Pro Arg Gln Pro Arg His Val Gly Asp Gly Val Ala Phe Gly Gln
                245                 250                 255

Phe Leu Asp Leu Gly Ser Ser Gly Gln Ile Asp Phe Asp Ala Ala Ala
            260                 265                 270

Ala Ala Phe Phe Pro Asn Leu Pro Ser Leu Pro Pro Thr Val Leu Pro
```

```
                275                 280                 285
Pro Pro Pro Ser Phe Ala Met Tyr Gly Gly Gly Ser Pro Ala Val Ser
    290                 295                 300

Val Trp Pro Phe Thr Leu
305                 310

<210> SEQ ID NO 20
<211> LENGTH: 334
<212> TYPE: PRT
<213> ORGANISM: Arabidopsis

<400> SEQUENCE: 20

Met Met Leu Ala Val Glu Asp Val Leu Ser Glu Leu Ala Gly Glu Glu
  1               5                  10                  15

Arg Asn Glu Arg Gly Leu Pro Pro Gly Phe Arg Phe His Pro Thr Asp
                 20                  25                  30

Glu Glu Leu Ile Thr Phe Tyr Leu Ala Ser Lys Ile Phe His Gly Gly
             35                  40                  45

Leu Ser Gly Ile His Ile Ser Glu Val Asp Leu Asn Arg Cys Glu Pro
 50                  55                  60

Trp Glu Leu Pro Glu Met Ala Lys Met Gly Glu Arg Glu Trp Tyr Phe
 65                  70                  75                  80

Tyr Ser Leu Arg Asp Arg Lys Tyr Pro Thr Gly Leu Arg Thr Asn Arg
                 85                  90                  95

Ala Thr Thr Ala Gly Tyr Trp Lys Ala Thr Gly Lys Asp Lys Glu Val
            100                 105                 110

Phe Ser Gly Gly Gly Gly Gln Leu Val Gly Met Lys Lys Thr Leu Val
        115                 120                 125

Phe Tyr Lys Gly Arg Ala Pro Arg Gly Leu Lys Thr Lys Trp Val Met
    130                 135                 140

His Glu Tyr Arg Leu Glu Asn Asp His Ser His Arg His Thr Cys Lys
145                 150                 155                 160

Glu Glu Trp Val Ile Cys Arg Val Phe Asn Lys Thr Gly Asp Arg Lys
                165                 170                 175

Asn Val Gly Leu Ile His Asn Gln Ile Ser Tyr Leu His Asn His Ser
            180                 185                 190

Leu Ser Thr Thr His His His His Glu Ala Leu Pro Leu Leu Ile
        195                 200                 205

Glu Pro Ser Asn Lys Thr Leu Thr Asn Phe Pro Ser Leu Leu Tyr Asp
    210                 215                 220

Asp Pro His Gln Asn Tyr Asn Asn Asn Phe Leu His Gly Ser Ser
225                 230                 235                 240

Gly His Asn Ile Asp Glu Leu Lys Ala Leu Ile Asn Pro Val Val Ser
                245                 250                 255

Gln Leu Asn Gly Ile Ile Phe Pro Ser Gly Asn Asn Asn Asp Glu
            260                 265                 270

Asp Asp Phe Asp Phe Asn Leu Gly Val Lys Thr Glu Gln Ser Ser Asn
        275                 280                 285

Gly Asn Glu Ile Asp Val Arg Asp Tyr Leu Glu Asn Pro Leu Phe Gln
    290                 295                 300

Glu Ala Ser Tyr Gly Leu Leu Gly Phe Ser Ser Ser Pro Gly Pro Leu
305                 310                 315                 320

His Met Leu Leu Asp Ser Pro Cys Pro Leu Gly Phe Gln Leu
                325                 330
```

<210> SEQ ID NO 21
<211> LENGTH: 324
<212> TYPE: PRT
<213> ORGANISM: Arabidopsis

<400> SEQUENCE: 21

```
Met Glu Thr Glu Glu Met Lys Glu Ser Ser Ile Ser Met Val Glu
 1               5                  10                  15

Ala Lys Leu Pro Pro Gly Phe Arg Phe His Pro Lys Asp Glu Leu
                20                  25                  30

Val Cys Asp Tyr Leu Met Arg Arg Ser Leu His Asn Asn His Arg Pro
                35                  40                  45

Pro Leu Val Leu Ile Gln Val Asp Leu Asn Lys Cys Glu Pro Trp Asp
 50                  55                  60

Ile Pro Lys Met Ala Cys Val Gly Gly Lys Asp Trp Tyr Phe Tyr Ser
 65                  70                  75                  80

Gln Arg Asp Arg Lys Tyr Ala Thr Gly Leu Arg Thr Asn Arg Ala Thr
                85                  90                  95

Ala Thr Gly Tyr Trp Lys Ala Thr Gly Lys Asp Arg Thr Ile Leu Arg
                100                 105                 110

Lys Gly Lys Leu Val Gly Met Arg Lys Thr Leu Val Phe Tyr Gln Gly
                115                 120                 125

Arg Ala Pro Arg Gly Arg Lys Thr Asp Trp Val Met His Glu Phe Arg
 130                 135                 140

Leu Gln Gly Ser His His Pro Asn His Ser Leu Ser Ser Pro Lys
 145                 150                 155                 160

Glu Asp Trp Val Leu Cys Arg Val Phe His Lys Asn Thr Glu Gly Val
                165                 170                 175

Ile Cys Arg Asp Asn Met Gly Ser Cys Phe Asp Glu Thr Ala Ser Ala
                180                 185                 190

Ser Leu Pro Pro Leu Met Asp Pro Tyr Ile Asn Phe Asp Gln Glu Pro
                195                 200                 205

Ser Ser Tyr Leu Ser Asp His His Tyr Ile Ile Asn Glu His Val
 210                 215                 220

Pro Cys Phe Ser Asn Leu Ser Gln Asn Gln Thr Leu Asn Ser Asn Leu
 225                 230                 235                 240

Thr Asn Ser Val Ser Glu Leu Lys Ile Pro Cys Lys Asn Pro Asn Pro
                245                 250                 255

Leu Phe Thr Gly Gly Ser Ala Ser Ala Thr Leu Thr Gly Leu Asp Ser
                260                 265                 270

Phe Cys Ser Ser Asp Gln Met Val Leu Arg Ala Leu Leu Ser Gln Leu
                275                 280                 285

Thr Lys Ile Asp Gly Ser Leu Gly Pro Lys Glu Ser Gln Ser Tyr Gly
                290                 295                 300

Glu Gly Ser Ser Glu Ser Leu Leu Thr Asp Ile Gly Ile Pro Ser Thr
 305                 310                 315                 320

Val Trp Asn Cys
```

<210> SEQ ID NO 22
<211> LENGTH: 343
<212> TYPE: PRT
<213> ORGANISM: Artificial Sequence
<220> FEATURE:
<223> OTHER INFORMATION: consensus
<220> FEATURE:
<221> NAME/KEY: VARIANT

```
<222> LOCATION: 1, 2, 3, 4, 5, 6, 7, 8, 9, 10, 11, 12, 13, 14, 15, 16,
      17, 18, 21, 37, 44, 46, 47, 48, 72, 106, 111, 113, 114, 115,
      116, 117, 118, 119, 120, 121, 139, 142, 151, 153, 154, 156,
      157, 158, 159, 160, 161, 162, 163, 164, 165, 166, 183
<223> OTHER INFORMATION: Xaa = Any Amino Acid
<220> FEATURE:
<221> NAME/KEY: VARIANT
<222> LOCATION: 184, 185, 186, 187, 188, 189, 190, 191, 192, 193, 194,
      195, 196, 197, 198, 199, 200, 201, 202, 203, 204, 205, 206, 207,
      208, 209, 210, 212, 213, 214, 215, 216, 217, 218, 219, 220,
      221, 222, 223, 224, 225, 226, 227, 228, 229, 230, 231
<223> OTHER INFORMATION: Xaa = Any Amino Acid
<220> FEATURE:
<221> NAME/KEY: VARIANT
<222> LOCATION: 232, 233, 234, 235, 236, 237, 238, 239, 240, 241, 242,
      243, 244, 245, 246, 247, 248, 249, 250, 251, 252, 253, 254, 255,
      256, 257, 258, 259, 260, 261, 262, 263, 264, 265, 266, 267,
      268, 269, 270, 271, 272, 273, 274, 275, 276, 277, 278
<223> OTHER INFORMATION: Xaa = Any Amino Acid
<220> FEATURE:
<221> NAME/KEY: VARIANT
<222> LOCATION: 279, 280, 281, 282, 283, 284, 285, 286, 287, 288, 289,
      290, 291, 292, 293, 294, 295, 296, 297, 298, 299, 300, 301, 302,
      303, 304, 305, 306, 307, 308, 309, 310, 311, 312, 313, 314,
      315, 316, 317, 318, 319, 320, 321, 322, 323, 324, 325
<223> OTHER INFORMATION: Xaa = Any Amino Acid
<220> FEATURE:
<221> NAME/KEY: VARIANT
<222> LOCATION: 326, 327, 328, 329, 330, 331, 332, 333, 334, 335, 336,
      337, 338, 339, 340, 341, 342, 343
<223> OTHER INFORMATION: Xaa = Any Amino Acid

<400> SEQUENCE: 22

Xaa Xaa Xaa Xaa Xaa Xaa Xaa Xaa Xaa Xaa Xaa Xaa Xaa Xaa Xaa
 1               5                  10                  15

Xaa Xaa Glu Leu Xaa Leu Pro Pro Gly Phe Arg Phe His Pro Thr Asp
            20                  25                  30

Glu Glu Leu Val Xaa His Tyr Leu Cys Arg Lys Xaa Ala Xaa Xaa Xaa
             35                  40                  45

Leu Val Pro Ile Ile Ala Glu Val Asp Leu Tyr Lys Phe Asp Pro Trp
 50                  55                  60

Leu Pro Glu Ala Leu Phe Gly Xaa Glu Lys Glu Trp Tyr Phe Phe Ser
65                  70                  75                  80

Pro Arg Asp Arg Lys Tyr Pro Asn Gly Ser Arg Pro Asn Arg Ala Ala
                85                  90                  95

Gly Ala Gly Tyr Trp Lys Ala Thr Gly Xaa Asp Lys Pro Ile Xaa Ser
            100                 105                 110

Xaa Xaa Xaa Xaa Xaa Xaa Xaa Xaa Val Gly Ile Lys Lys Ala Leu
            115                 120                 125

Val Phe Tyr Ala Gly Lys Ala Pro Lys Gly Xaa Lys Thr Xaa Trp Ile
            130                 135                 140

Met His Glu Tyr Arg Leu Xaa Asp Xaa Xaa Arg Xaa Xaa Xaa Xaa Xaa
145                 150                 155                 160

Xaa Xaa Xaa Xaa Xaa Xaa Ser Leu Arg Leu Asp Asp Trp Val Leu Cys
            165                 170                 175

Arg Ile Tyr Asn Lys Lys Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Leu Xaa Xaa Xaa Xaa Xaa Xaa Xaa Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa
            340
```